(12) United States Patent
Kural

(10) Patent No.: US 11,837,328 B2
(45) Date of Patent: *Dec. 5, 2023

(54) METHODS AND SYSTEMS FOR DETECTING SEQUENCE VARIANTS

(71) Applicant: Seven Bridges Genomics Inc., Charlestown, MA (US)

(72) Inventor: Deniz Kural, Somerville, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,260

(22) Filed: Sep. 19, 2022

(65) Prior Publication Data
US 2023/0044434 A1   Feb. 9, 2023

Related U.S. Application Data

(63) Continuation of application No. 16/443,402, filed on Jun. 17, 2019, now Pat. No. 11,488,688, which is a (Continued)

(51) Int. Cl.
*G16B 30/10*   (2019.01)
*G16B 30/00*   (2019.01)
(Continued)

(52) U.S. Cl.
CPC .............. *G16B 30/10* (2019.02); *G16B 30/00* (2019.02); *G16B 30/20* (2019.02); *G16B 50/00* (2019.02)

(58) Field of Classification Search
None
See application file for complete search history.

(56) References Cited

U.S. PATENT DOCUMENTS

| 5,511,158 A | 4/1996 | Sims |
| 5,701,256 A | 12/1997 | Marr et al. |

(Continued)

FOREIGN PATENT DOCUMENTS

| CA | 2 869 574 A1 | 10/2013 |
| EP | 3053073 B1 | 7/2019 |

(Continued)

OTHER PUBLICATIONS

Exam Report issued in EP14803268.3 dated Apr. 21, 2017.
(Continued)

*Primary Examiner* — Hung Q Dang
(74) *Attorney, Agent, or Firm* — Wolf, Greenfield & Sacks, P.C.

(57) ABSTRACT

The invention provides methods for identifying rare variants near a structural variation in a genetic sequence, for example, in a nucleic acid sample taken from a subject. The invention additionally includes methods for aligning reads (e.g., nucleic acid reads) to a reference sequence construct accounting for the structural variation, methods for building a reference sequence construct accounting for the structural variation or the structural variation and the rare variant, and systems that use the alignment methods to identify rare variants. The method is scalable, and can be used to align millions of reads to a construct thousands of bases long, or longer.

20 Claims, 9 Drawing Sheets

Specification includes a Sequence Listing.

Reference Sequence (Start)

SEQ ID NO. 1

Incorporate Deletion "AG"

SEQ ID NO. 1

SEQ ID NO. 1 & 2

Related U.S. Application Data continuation of application No. 15/906,404, filed on Feb. 27, 2018, now Pat. No. 10,325,675, which is a continuation of application No. 15/196,345, filed on Jun. 29, 2016, now Pat. No. 9,904,763, which is a continuation of application No. 14/811,057, filed on Jul. 28, 2015, now Pat. No. 9,390,226, which is a continuation of application No. 14/041,850, filed on Sep. 30, 2013, now Pat. No. 9,116,866.

(60) Provisional application No. 61/884,380, filed on Sep. 30, 2013, provisional application No. 61/868,249, filed on Aug. 21, 2013.

(51) Int. Cl.
*G16B 30/20* (2019.01)
*G16B 50/00* (2019.01)

(56) References Cited

U.S. PATENT DOCUMENTS

| | | | |
|---|---|---|---|
| 6,054,278 | A | 4/2000 | Dodge et al. |
| 6,223,128 | B1 | 4/2001 | Allex et al. |
| 7,577,554 | B2 | 8/2009 | Lystad et al. |
| 7,580,918 | B2 | 8/2009 | Chang et al. |
| 7,809,509 | B2 | 10/2010 | Milosavljevic |
| 7,885,840 | B2 | 2/2011 | Sadiq et al. |
| 7,917,302 | B2 | 3/2011 | Rognes |
| 8,209,130 | B1 | 6/2012 | Kennedy et al. |
| 8,340,914 | B2 | 12/2012 | Gatewood et al. |
| 8,370,079 | B2 | 2/2013 | Sorenson et al. |
| 8,639,847 | B2 | 1/2014 | Blaszczak et al. |
| 9,063,914 | B2 | 6/2015 | Kural et al. |
| 9,092,402 | B2 | 7/2015 | Kural et al. |
| 9,116,866 | B2 | 8/2015 | Kural |
| 9,390,226 | B2 | 7/2016 | Kural |
| 9,817,944 | B2 | 11/2017 | Kural |
| 9,904,763 | B2 | 2/2018 | Kural |
| 10,325,675 | B2 | 6/2019 | Kural |
| 2004/0023209 | A1 | 2/2004 | Jonasson |
| 2005/0089906 | A1 | 4/2005 | Furuta et al. |
| 2006/0292611 | A1 | 12/2006 | Berka et al. |
| 2007/0166707 | A1 | 7/2007 | Schadt et al. |
| 2008/0077607 | A1 | 3/2008 | Gatawood et al. |
| 2008/0294403 | A1 | 11/2008 | Zhu et al. |
| 2009/0119313 | A1 | 5/2009 | Pearce |
| 2009/0164135 | A1 | 6/2009 | Brodzik et al. |
| 2009/0300781 | A1 | 12/2009 | Bancroft et al. |
| 2010/0041048 | A1 | 2/2010 | Diehl et al. |
| 2010/0169026 | A1 | 7/2010 | Sorenson et al. |
| 2011/0004413 | A1 | 1/2011 | Carnevali et al. |
| 2011/0096193 | A1 | 4/2011 | Egawa |
| 2011/0098193 | A1 | 4/2011 | Kingsmore et al. |
| 2011/0295514 | A1 | 12/2011 | Breu et al. |
| 2012/0041727 | A1 | 2/2012 | Mishra et al. |
| 2012/0045771 | A1 | 2/2012 | Beier et al. |
| 2012/0239706 | A1 | 9/2012 | Steinfadt | |
| 2012/0330566 | A1* | 12/2012 | Chaisson ............... G16B 30/10 702/20 |
| 2013/0059738 | A1 | 3/2013 | Leamon et al. |
| 2013/0059740 | A1 | 3/2013 | Drmanac et al. |
| 2013/0073214 | A1 | 3/2013 | Hyland et al. |
| 2013/0103320 | A1* | 4/2013 | Dzakula ............... G16B 30/10 702/19 |
| 2013/0124100 | A1 | 5/2013 | Drmanac et al. |
| 2013/0289099 | A1 | 10/2013 | Goff et al. |
| 2013/0311106 | A1 | 11/2013 | White et al. |
| 2014/0025312 | A1 | 1/2014 | Chin et al. |
| 2014/0051588 | A9 | 2/2014 | Drmanac et al. |
| 2014/0052381 | A1* | 2/2014 | Utiramerur ............ G16B 30/00 702/19 |
| 2014/0066317 | A1 | 3/2014 | Talasaz |
| 2014/0100792 | A1 | 4/2014 | Deciu et al. |
| 2014/0136120 | A1 | 5/2014 | Colwell et al. |
| 2014/0180594 | A1 | 6/2014 | Kim et al. |
| 2014/0200147 | A1 | 7/2014 | Bartha et al. |
| 2014/0278590 | A1 | 9/2014 | Abbassi et al. |
| 2014/0280360 | A1 | 9/2014 | Webber et al. |
| 2014/0323320 | A1 | 10/2014 | Jia et al. |
| 2015/0056613 | A1 | 2/2015 | Kural |
| 2015/0057946 | A1 | 2/2015 | Kural |
| 2015/0094212 | A1 | 4/2015 | Gottimukkala et al. |
| 2015/0110754 | A1 | 4/2015 | Bai et al. |
| 2015/0112602 | A1 | 4/2015 | Kural et al. |
| 2015/0112658 | A1 | 4/2015 | Kural et al. |
| 2015/0197815 | A1 | 7/2015 | Kural |
| 2015/0199472 | A1 | 7/2015 | Kural |
| 2015/0199473 | A1 | 7/2015 | Kural |
| 2015/0199474 | A1 | 7/2015 | Kural |
| 2015/0199475 | A1 | 7/2015 | Kural |
| 2015/0227685 | A1 | 8/2015 | Kural |
| 2015/0293994 | A1 | 10/2015 | Kelly |
| 2015/0302145 | A1 | 10/2015 | Kural et al. |
| 2015/0310167 | A1 | 10/2015 | Kural et al. |
| 2015/0344970 | A1 | 12/2015 | Vogelstein et al. |
| 2015/0347678 | A1 | 12/2015 | Kural |
| 2015/0356147 | A1 | 12/2015 | Mishra et al. |
| 2016/0259880 | A1 | 9/2016 | Semenyuk |
| 2016/0306921 | A1 | 10/2016 | Kural |
| 2016/0364523 | A1 | 12/2016 | Locke et al. |
| 2017/0053341 | A1 | 2/2017 | Locke et al. |
| 2017/0058320 | A1 | 3/2017 | Locke et al. |
| 2017/0058365 | A1 | 3/2017 | Locke et al. |
| 2017/0193351 | A1 | 7/2017 | Noyes et al. |
| 2017/0199959 | A1 | 7/2017 | Locke |
| 2017/0199960 | A1 | 7/2017 | Ghose et al. |
| 2017/0242958 | A1 | 8/2017 | Brown |
| 2018/0336314 | A1 | 11/2018 | Kural |
| 2020/0168295 | A1 | 5/2020 | Kural |

FOREIGN PATENT DOCUMENTS

| | | | | |
|---|---|---|---|---|
| WO | WO 2012/096579 | A2 | 7/2012 | |
| WO | WO 2012/098515 | A1 | 7/2012 | |
| WO | WO 2012/142531 | A2 | 10/2012 | |
| WO | WO-2013151803 | A1 * | 10/2013 | ........... C12Q 1/6869 |
| WO | WO 2015/027050 | A1 | 2/2015 | |
| WO | WO 2015/048753 | A1 | 4/2015 | |
| WO | WO 2015/058093 | A1 | 4/2015 | |
| WO | WO 2015/058095 | A1 | 4/2015 | |
| WO | WO 2015/058097 | A1 | 4/2015 | |
| WO | WO 2015/058120 | A1 | 4/2015 | |
| WO | WO 2015/061099 | A1 | 4/2015 | |
| WO | WO 2015/061103 | A1 | 4/2015 | |
| WO | WO 2015/105963 | A1 | 7/2015 | |
| WO | WO 2015/123269 | A1 | 8/2015 | |
| WO | WO 2016/141294 | A1 | 9/2016 | |
| WO | WO 2016/201215 | A1 | 12/2016 | |
| WO | WO 2017/120128 | A1 | 7/2017 | |
| WO | WO 2017/123864 | A1 | 7/2017 | |
| WO | WO 2017/147124 | A1 | 8/2017 | |

OTHER PUBLICATIONS

Examination Report issued in SG 11201601124Y, dated Mar. 1, 2018.
Extended European Search Report issued in EP 14837955.5 dated Mar. 29, 2017.
Extended European Search Report issued in EP 14847490.1 dated May 9, 2017.
Extended European Search Report issued in EP 14854801.9 dated Apr. 12, 2017.
International Search Report and Written Opinion for International Application No. PCT/US2017/018830 dated Aug. 31, 2017.
International Search Report and Written Opinion for International Application No. PCT/US2015/010604 dated Mar. 31, 2015.
International Search Report and Written Opinion for International Application No. PCT/US2017/012015 dated Apr. 19, 2017.
International Search Report and Written Opinion for International Application No. PCT/US2014/061156 dated Feb. 17, 2015.

(56) References Cited

OTHER PUBLICATIONS

International Search Report and Written Opinion for International Application No. PCT/US2016/057324 dated Jan. 10, 2017.
International Search Report and Written Opinion for International Application No. PCT/US2014/061162 dated Mar. 19, 2015.
International Search Report and Written Opinion for International Application No. PCT/US2015/015375 dated May 11, 2015.
International Search Report and Written Opinion for International Application No. PCT/US2016/020899 dated May 5, 2016.
International Search Report and Written Opinion for International Application No. PCT/US2017/013329 dated Apr. 7, 2017.
International Search Report and Written Opinion for International Application No. PCT/US2014/052065 dated Dec. 11, 2014.
International Search Report and Written Opinion for International Application No. PCT/US2014/058328, dated Dec. 30, 2014.
International Search Report and Written Opinion for International Application No. PCT/US2014/061198, dated Feb. 4, 2015.
International Search Report and Written Opinion for International Application No. PCT/US2014/060690 dated Feb. 10, 2015.
International Search Report and Written Opinion for International Application No. PCT/US2014/061158 dated Feb. 4, 2015.
International Search Report and Written Opinion for International Application No. PCT/US2014/060680 dated Jan. 27, 2015.
International Search Report and Written Opinion for International Application No. PCT/US2016/033201 dated Sep. 2, 2016.
International Search Report and Written Opinion for International Application No. PCT/US2016/036873 dated Sep. 7, 2016.
Written Opinion issued in SG 11201601124Y dated Dec. 21, 2016.
Written Opinion issued in SG 11201602903X dated May 29, 2017.
Written Opinion issued in SG 11201603039P dated Jun. 12, 2017.
Written Opinion issued in SG 11201603044S dated Sep. 10, 2017.
Written Opinion issued in SG 11201605506Q dated Jun. 15, 2017.
Agarwal, 2013, SINNET: Social interaction Network Extractorfrom Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13): i352-i360.
Airoldi, 2008, Mixed membership stochastic blockmodels, JMLR 9:1981-2014.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioninformatics 29 (10):1250-1259.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Berlin, 2014, Assembling large genomes with single-molecule sequencing and locality sensitive hashing, bioRxiv preprint (35 pages); retrieved from the internet on Jan. 29, 2015.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.

Browning et al, Haplotype phasing: existing methods and new developments, 2011, vol. 12, Nature Reviews Genetics, pp. 703-714.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Chang, 2005, The application of alternative splicing graphs in quantitative analysis of alternative splicing form from EST database, Int J Comp Appl Tech 22(1):14.
Chen et al., Transient hypermutability, chromothripsis and replication-based mechanisms in the generation of concurrent clustered mutations. Mutation Research/Reviews in Mutation Research. Jan. 1, 2012;750(1):52-9.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Compeau, 2011, How to apply de Bruijn graphs to genome assembly, Nat Biotech 29(11):987-991.
Craig, 1990, Ordering of cosmid clones covering the Herpes simplex virus type I (HSV-I) genome: a test case for fingerprinting by hybridisation, Nucleic Acids Research 18:9 pp. 2653-2660.
Danecek et al., The variant call format and VCFtools. Bioinformatics. Aug. 1, 2011;27(15):2156-8.
Denoeud, 2004, Identification of polymorphic tandem repeats by direct comparison of genome sequence from different bacterial strains: a web-based resource, BMC Bioinformatics 5:4 pp. 1-12.
DePristo, 2011, A framework for variation discovery and genotyping using next-generation DNA sequencing data, Nat Gen 43:491-498.
Duan et al., Optimizing de novo common wheat transcriptome assembly using short-read RNA-Seq data. (2012) pp. 1-12, vol. 13, BMC Genomics.
Dudley, 2009, A quick guide for developing effective bioinformatics programming skills, PLoS Comput Biol 5(12): e1000589.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fitch, 1970, Distinguishing homologous from analogous proteins, Systematic Zoology 19:99-113.
Flicek, 2009, Sense from sequence reads: methods for alignment and assembly, Nat Meth Supp; 6(11s):s6-s12.
Garber, 2011, Computational methods for transcriptorne annotation and quantification using RNA-Seq, Nat Meth 8(6):469-477.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Gotoh, 1982, An improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Grasso, 2004, Combining partial order alignment and progressive multiple sequence alignment increases alignment speed and scalability to very large alignment problems, Bioinformatics 20(10):1546-1556.
Guttman 2010, Ab initio reconstruction of cell type-specific transcriptomes in mouse reveals the conserved multi-exonic structure of lincRNAs, Nat Biotech 28(5):503-510.
Guttman; 2010, Ab initio reconstruction of transcriptomes of pluripotent and lineage committed cells reveals gene structures of thousands of lincRNAs, NIH-PA Author Manuscript.

(56) References Cited

OTHER PUBLICATIONS

Haas, 2004, DAGchainer: a tool for mining segmental genome duplications and synteny, Bioinformatics 20(18):3643-3646.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol. Evol 6(6), pp. 669-684.
Homer, 2010, Improved variant discovery through local re-alignment of short-read next generation sequencing data using SRMA, Genome Biol 11(10):R99.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002, pp. 45-69.
Hutchinson, 2014, Allele-specific methylation occurs at genetic variants associated with complex diseases, PLoS One 9(6):e98464.
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptorne data, BMC Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal Wand Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
LeGault, 2010, Learning Probalistic Splice Graphs from RNA-Seq data, pages.cs.wisc.edu/.about.legault/cs760_writeup.pdf; retrieved from the internet on Apr. 6, 2014.
LeGault, 2013, Inference of alternative splicing from RNA-Seq data with probabilistic splice araphs, Bioinformatics 29(18):2300-2310.
Leipzig, 2004, The alternative splicing gallery (ASG): Bridging the gap between genome and transcriptome, Nuc Acids Res 23(13):3977-3983.
Li et al., Mapping short DNA sequencing reads and calling variants using mapping quality scores. Genome research. Nov. 1, 2008;18(11):1851-8.
Li, 2009, Fast and accurate short read alignment with Burrows-Wheeler Transform. Bioinforrnatics 25:1754-60.
Li, 2010, A survey of sequence alignment algorithms for next-generation sequencing, Briefings in Bionformatics 11(5):473-483.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Bioinf 12:10.
Lupski, 2005, Genomic disorders: Molecular mechanisms for rearrangements and conveyed phenotypes, PLoS Genetics 1(6):e49.
Ma, 2010, Multiple genome alignment based on longest path in directed acyclic graphs, Int J Bioinformatics 6(4):366-683.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived fromthe internet on Jun. 3, 2016.
Marth et al., 1999—A general approach to single-nucleotide polymorphism discovery, pp. 452-456, vol. 23, Nature Genetics.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Mount, 2001, Multiple Sequence Alignment, Bioinformatics, 2001, Cold Spring Harbor Laboratory Press, Cold Spring Harbor, New York, pp. 139-204.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Nagarajan, 2013, Sequence assembly demystified, Nat Rev 14:157-167.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Newman, 2013, Community detection and graph portioning, Europhys Lett 103(2):28003, arXiv:1305.4974v1.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease. EMBO Molecular Medicine 7:8 1034-1047.
Oshiack, 2010, From RNA-seq reads to differential expression results. Genome Bio 11:220.
Parks, 2015, Detecting non-allelic homologous recombination from high-throughput sequencing data, Genome Biol 16:17.
Peixoto, 2014, Efficient Monte Carlo and greedy heuristic for the inference of stochastic block models, Phys. Rev. E 89, 012804.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Rajaram, 2013, Pearl millet [*Pennisetum glaucum* (L.) R. Br.] consensus linkage map constructed using four RIL mapping populations and newly developed EST-SSRs, BMC Genomics 14(1):159.

(56) References Cited

OTHER PUBLICATIONS

Raphael, 2004; A novel method for multiple alignment of sequences with repeated and shuffled elements, Genome Res 14:2336-2346.
Robertson, 2010, De novo assembly and analysis of RNA-seg data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches; Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Orneag, Mol Syst Biol 7:539.
Slater, 2005, Automated generation of heuristics for biological sequence comparison, BMC Bioinformatics 6:31.
Smith, 2012, Multiple insert size paired-end sequencing for deconvolution of complex transcriptions, RNA Bio 9(5)596-609.
Sosa, 2012, Next-Generation Sequencing of Human Mitochondrial Reference Genomes Uncovers High Heteroplasmy Frequency, PLoS One 8(10):e1002737.
Sturgeon, RCDA: a highly sensitive and specific alternatively spliced transcript assembly tool featuring upstream consecutive exon structures, Genomics, Dec. 2012, 100(6): 357-362.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016, at.
Szaikowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Wang, 2009, RNA-Seq: a revolutionary tool for transcriptomics, Nat Rev Genet 10(1):57-63.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yanovsky, 2008, Read mapping algorithms for single molecule sequencing data, Proc 8th Int Workshop Alg Bioinformatics 5251:38-49.
Yu, 2010, The construction of a tetraploid cotton genome wide comprehensive reference map, Genomics 95:230-240.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.
U.S. Appl. No. 14/041,850, filed Sep. 30, 2013, Kural.
U.S. Appl. No. 14/811,057, filed Jul. 28, 2015, Kural.
U.S. Appl. No. 15/196,345, filed Jun. 29, 2016, Kural.
U.S. Appl. No. 15/906,404, filed Feb. 27, 2018, Kural.
U.S. Appl. No. 16/443,402, filed Jun. 17, 2019, Kural.
PCT/US2016/033201, Sep. 2, 2016, International Search Report and Written Opinion.
PCT/US2014/061158, Feb. 4, 2015, International Search Report and Written Opinion.
EP14847490.1, May 9, 2017, Extended European Search Report and Written Opinion.
PCT/US2014/058328, Dec. 30, 2014, International Search Report and Written Opinion.
PCT/US2014/061198, Feb. 4, 2015, International Search Report and Written Opinion.
EP14803268.3, Apr. 21, 2017, Exam Report.
SG11201603039P, Jun. 12, 2017, Written Opinion.
PCT/US2014/061162, Mar. 19, 2015, International Search Report and Written Opinion.
PCT/US2016/057324, Jan. 10, 2017, International Search Report and Written Opinion.
PCT/US2016/036873, Sep. 7, 2016, International Search Report and Written Opinion.
EP14854801.9, Apr. 12, 2017, Extended European Search Report and Written Opinion.
SG11201602903X, May 29, 2017, Written Opinion.
PCT/US2014/061156, Feb. 17, 2015, International Search Report and Written Opinion.
EP14837955.5, Mar. 29, 2017, Extended European Search Report and Written Opinion.
SG11201601124Y, Mar. 1, 2018, Examination Report.
SG11201601124Y, Dec. 21, 2016, Written Opinion.
PCT/US2014/052065, Dec. 11, 2014, International Search Report and Written Opinion.
PCT/US2014/060680, Jan. 27, 2015, International Search Report and Written Opinion.
SG11201603044S, Sep. 10, 2017, Written Opinion.
PCT/US2014/060690, Feb. 10, 2015, International Search Report and Written Opinion.
SG11201605506Q, Jun. 15, 2017, Written Opinion.
PCT/US2015/010604, Mar. 31, 2015, International Search Report and Written Opinion.
PCT/US2015/015375, May 11, 2015, International Search Report and Written Opinion.
PCT/US2016/020899, May 5, 2016, International Search Report and Written Opinion.
PCT/US2017/013329, Apr. 7, 2017, International Search Report and Written Opinion.
PCT/US2017/012015, Apr. 19, 2017, International Search Report and Written Opinion.

(56) References Cited

OTHER PUBLICATIONS

PCT/US2017/018830, Jun. 14, 2017, International Search Report and Written Opinion.

\* cited by examiner

FIG. 6A

Hypothetical Sequences

S    GGGGCTTATCCTGCGTCCCAGGGCGAGGACCGCTTGGTTCGAATCTGGG    SEQ ID NO. 14
                        20th  23rd  26th        34th              50th

S*   GGGGCTTATCCTGCGTCCCAGGGCGCTTATGATGAATGTCGACAATGCAA    SEQ ID NO. 15

S**  GGGGCTTATCCTGCGTCCCAGGGCGCTTATGATGAATGTCGACAATGCAA    SEQ ID NO. 16

Read 1 of S**    AGGTCGCTTATGATG    SEQ ID NO. 17

FIG. 6B

Alignment of Read 1 to Linear Reference Sequence

Read 1 of S**   AGGTCGCTTATGATG    SEQ ID NO. 17

S    GGGGCTTATCCTGCGTCCCAGGGCGAGGACCGCTTGGTTCGAATCTGGG    SEQ ID NO. 14

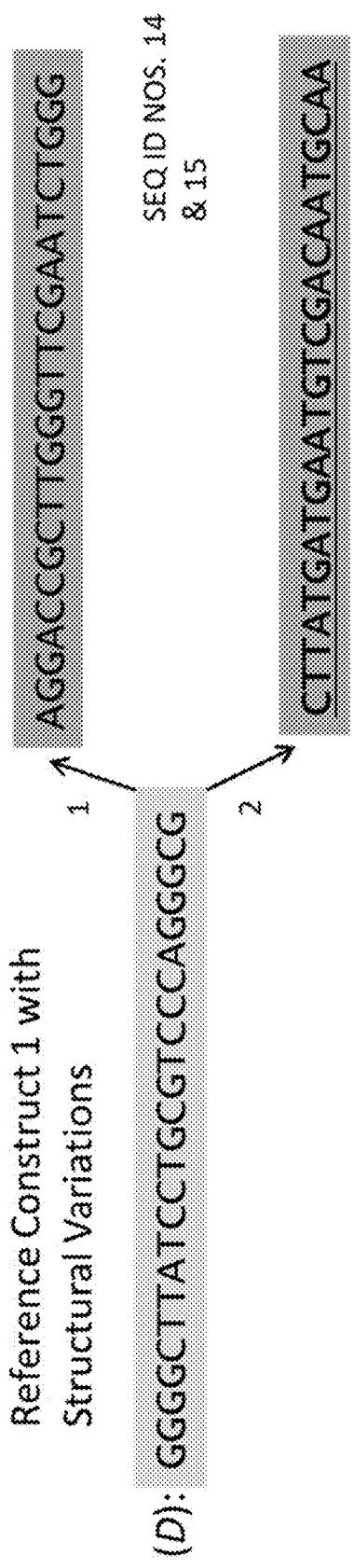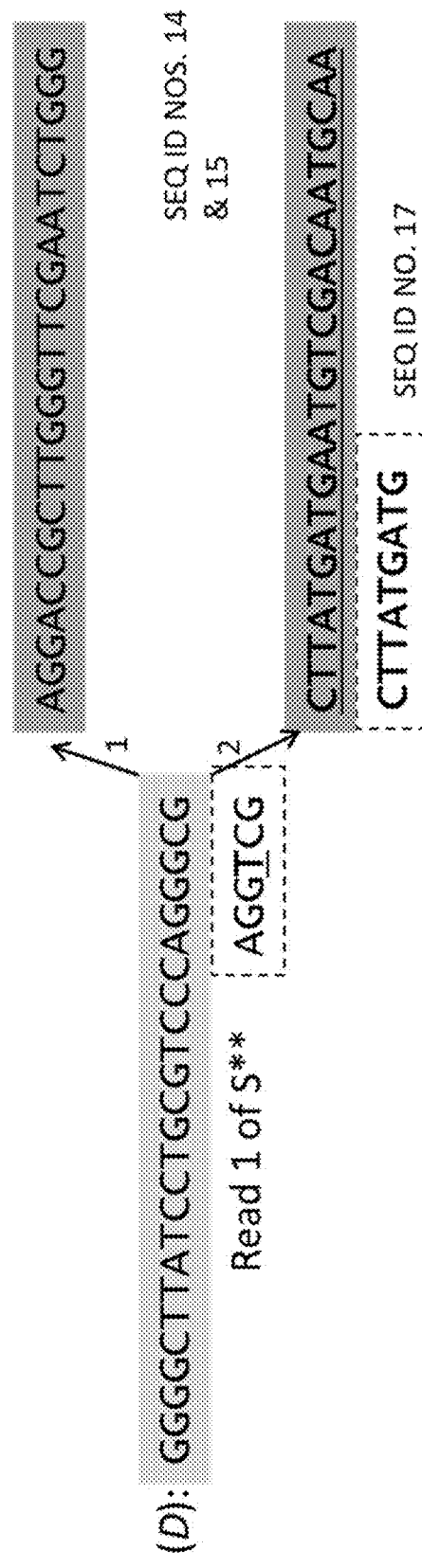

SEQUENCE LISTING

```
Sequence total quantity: 17
SEQ ID NO: 1            moltype = DNA  length = 27
FEATURE                 Location/Qualifiers
misc_feature            1..27
                        note = Synthetic Sequence
source                  1..27
                        mol_type = other DNA
                        organism = synthetic construct
SEQUENCE: 1
catagtacct aggtcttgga gctagtc                                      27

SEQ ID NO: 2            moltype = DNA  length = 25
FEATURE                 Location/Qualifiers
misc_feature            1..25
                        note = Synthetic Sequence
```

```
source                   1..25
                         mol_type = other DNA
                         organism = synthetic construct
SEQUENCE: 2
catagtacct aggtcttggc tagtc                                          25

SEQ ID NO: 3             moltype = DNA   length = 27
FEATURE                  Location/Qualifiers
misc_feature             1..27
                         note = Synthetic Sequence
source                   1..27
                         mol_type = other DNA
                         organism = synthetic construct
SEQUENCE: 3
catagtacct aggggtcttg gctagtc                                        27

SEQ ID NO: 4             moltype = DNA   length = 29
FEATURE                  Location/Qualifiers
misc_feature             1..29
                         note = Synthetic Sequence
source                   1..29
                         mol_type = other DNA
                         organism = synthetic construct
SEQUENCE: 4
catagtacct aggggtcttg gagctagtc                                      29

SEQ ID NO: 5             moltype = DNA   length = 25
FEATURE                  Location/Qualifiers
misc_feature             1..25
                         note = Synthetic Sequence
source                   1..25
                         mol_type = other DNA
                         organism = synthetic construct
SEQUENCE: 5
cataggacct aggtcttggc tagtc                                          25

SEQ ID NO: 6             moltype = DNA   length = 27
FEATURE                  Location/Qualifiers
misc_feature             1..27
                         note = Synthetic Sequence
source                   1..27
                         mol_type = other DNA
                         organism = synthetic construct
SEQUENCE: 6
cataggacct aggtcttgga gctagtc                                        27

SEQ ID NO: 7             moltype = DNA   length = 27
FEATURE                  Location/Qualifiers
misc_feature             1..27
                         note = Synthetic Sequence
source                   1..27
                         mol_type = other DNA
                         organism = synthetic construct
SEQUENCE: 7
cataggacct aggggtcttg gctagtc                                        27

SEQ ID NO: 8             moltype = DNA   length = 29
FEATURE                  Location/Qualifiers
misc_feature             1..29
                         note = Synthetic Sequence
source                   1..29
                         mol_type = other DNA
                         organism = synthetic construct
SEQUENCE: 8
cataggacct aggggtcttg gagctagtc                                      29

SEQ ID NO: 9             moltype = DNA   length = 12
FEATURE                  Location/Qualifiers
misc_feature             1..12
                         note = Synthetic Sequence
source                   1..12
                         mol_type = other DNA
                         organism = synthetic construct
SEQUENCE: 9
ggatcgaaat gg                                                        12
```

```
SEQ ID NO: 10              moltype = DNA  length = 17
FEATURE                    Location/Qualifiers
misc_feature               1..17
                           note = Synthetic Sequence
source                     1..17
                           mol_type = other DNA
                           organism = synthetic construct
SEQUENCE: 10
ttggatcgaa ttatggg                                                   17

SEQ ID NO: 11              moltype = DNA  length = 11
FEATURE                    Location/Qualifiers
misc_feature               1..11
                           note = Synthetic Sequence
source                     1..11
                           mol_type = other DNA
                           organism = synthetic construct
SEQUENCE: 11
ttggatatgg g                                                         11

SEQ ID NO: 12              moltype = DNA  length = 16
FEATURE                    Location/Qualifiers
misc_feature               1..16
                           note = Synthetic Sequence
source                     1..16
                           mol_type = other DNA
                           organism = synthetic construct
SEQUENCE: 12
agctacgtac actacc                                                    16

SEQ ID NO: 13              moltype = DNA  length = 15
FEATURE                    Location/Qualifiers
misc_feature               1..15
                           note = Synthetic Sequence
source                     1..15
                           mol_type = other DNA
                           organism = synthetic construct
SEQUENCE: 13
agctatcgta ctagc                                                     15

SEQ ID NO: 14              moltype = DNA  length = 50
FEATURE                    Location/Qualifiers
misc_feature               1..50
                           note = Synthetic Sequence
source                     1..50
                           mol_type = other DNA
                           organism = synthetic construct
SEQUENCE: 14
ggggcttatc ctgcgtccca gggcgaggac cgcttgggtt cgaatctggg               50

SEQ ID NO: 15              moltype = DNA  length = 50
FEATURE                    Location/Qualifiers
misc_feature               1..50
                           note = Synthetic Sequence
source                     1..50
                           mol_type = other DNA
                           organism = synthetic construct
SEQUENCE: 15
ggggcttatc ctgcgtccca gggcgcttat gatgaatgtc gacaatgcaa               50

SEQ ID NO: 16              moltype = DNA  length = 50
FEATURE                    Location/Qualifiers
misc_feature               1..50
                           note = Synthetic Sequence
source                     1..50
                           mol_type = other DNA
                           organism = synthetic construct
SEQUENCE: 16
ggggcttatc ctgcgtccca ggtcgcttat gatgaatgtc gacaatgcaa               50
```

```
SEQ ID NO: 17          moltype = DNA  length = 15
FEATURE                Location/Qualifiers
misc_feature           1..15
                       note = Synthetic Sequence
source                 1..15
                       mol_type = other DNA
                       organism = synthetic construct
SEQUENCE: 17
aggtcgctta tgatg                                                        15
```

METHODS AND SYSTEMS FOR DETECTING SEQUENCE VARIANTS

RELATED APPLICATIONS

This application claims the benefit under 35 U.S.C. § 120 and is a continuation of U.S. Patent application Ser. No. 16/443,402, filed Jun. 17, 2019, entitled "METHODS AND SYSTEMS FOR DETECTING SEQUENCE VARIANTS", which claims the benefit under 35 U.S.C. § 120 and is a continuation of U.S. patent application Ser. No. 15/906,404, filed Feb. 27, 2018, entitled "METHODS AND SYSTEMS FOR DETECTING SEQUENCE VARIANTS", which claims the benefit under 35 U.S.C. § 120 and is a continuation of U.S. patent application Ser. No. 15/196,345, filed Jun. 29, 2016, entitled "METHODS AND SYSTEMS FOR DETECTING SEQUENCE VARIANTS", which claims the benefit under 35 U.S.C. § 120 and is a continuation of U.S. patent application Ser. No. 14/811,057, filed Jul. 28, 2015, entitled "METHODS AND SYSTEMS FOR DETECTING SEQUENCE VARIANTS", which claims the benefit under 35 U.S.C. § 120 and is a continuation of U.S. patent application Ser. No. 14/041,850, filed Sep. 30, 2013, entitled "METHODS AND SYSTEM FOR DETECTING SEQUENCE VARIANTS", which claims priority under 35 U.S.C. § 119 to U.S. provisional Patent Application No. 61/868,249, filed Aug. 21, 2013, entitled, "METHODS AND SYSTEMS FOR ALIGNING SEQUENCES" and claims priority under 35 U.S.C. § 119 to U.S. provisional Patent Application No. 61/884,380, filed Sep. 30, 2013, entitled, "METHODS AND SYSTEM FOR DETECTING SEQUENCE VARIANTS", each of which is incorporated by reference in their entireties.

SEQUENCE LISTING

The contents of the electronic sequence listing (S196170006US06-SEQ-DGR.xml; Size: 22,591 bytes; and Date of Creation: Sep. 13, 2022) is herein incorporated by reference in its entirety.

FIELD OF THE INVENTION

The invention relates to methods and systems for aligning sequences (e.g., nucleic acid sequences) to each other to produce a continuous sequence read corresponding to a sample (e.g., genetic sample). The invention additionally relates to methods for identifying variants in the samples.

BACKGROUND

Genetics has evolved from an analytical science to an information science. Whereas scientists previously struggled with how to extract and identify nucleic acids, such techniques are now trivial. Next-generation sequencing (e.g., whole-transcriptome shotgun sequencing, pyrosequencing, ion semiconductor sequencing, sequencing by synthesis) can generate millions of reads, covering an entire genome, in just a few days. To achieve this throughput, NGS sequencing uses massive parallelization on smaller nucleic acid sequences that together make up a larger body of genetic information, e.g., a chromosome or a genome. Starting from a genetic sample, the nucleic acids (e.g., DNA) are broken up, amplified, and read with extreme speed. In light of these capabilities, scientists now struggle with how to (inexpensively) align the reads to identify loci in the sequence that indicate a disease or a risk of a disease.

State-of-the-art alignment methods use massive computing power to align overlapping reads to a reference to produce a sequence that can be probed for important genetic or structural information (e.g., biomarkers for disease). Ultimately, the goal of sequence alignment is to combine the set of nucleic acid reads produced by the sequencer to achieve a longer read (i.e., a contig) or even the entire genome of the subject based upon a genetic sample from that subject. Because the sequence data from next generation sequencers often comprises millions of shorter sequences that together represent the totality of the target sequence, aligning the reads is complex and computationally expensive. Additionally, in order to minimize sequence distortions caused by random sequencing errors (i.e., incorrect sequencing machine outputs), each portion of the probed sequence is sequenced multiple times (e.g., 2 to 100 times, or more) to minimize the influence of any random sequencing errors on the final alignments and output sequences generated. Finally, once all of the data corresponding to all of the nucleic acid reads is collected, the reads are aligned against a single reference sequence, e.g., GRCh37, in order to determine all (or some part of) the subject's sequence. In many instances, the individual reads are not actually displayed, but rather an aligned sequence is assembled into a sequence, and the sequence is provided as a data file.

Typically a sequence alignment is constructed by aggregating pairwise alignments between two linear strings of sequence information. As an example of alignment, two strings, S1 (SEQ ID NO. 12: AGCTACGTACACTACC) and S2 (SEQ ID NO. 13: AGCTATCGTACTAGC) can be aligned against each other. S1 typically corresponds to a read and S2 correspond to a portion of the reference sequence. With respect to each other, S1 and S2 can consist of substitutions, deletions, and insertions. Typically, the terms are defined with regard to transforming string S1 into string S2: a substitution occurs when a letter or sequence in S2 is replaced by a different letter or sequence of the same length in S1, a deletion occurs when a letter or sequence in S2 is "skipped" in the corresponding section of S1, and an insertion occurs when a letter or sequence occurs in S1 between two positions that are adjacent in S2. For example, the two sequences S1 and S2 can be aligned as below. The alignment below represents thirteen matches, a deletion of length one, an insertion of length two, and one substitution:

```
(S1)
                                           (SEQ ID NO. 12)
AGCTA-CGTACACTACC (S2)
                                           (SEQ ID NO. 13)
AGCTATCGTAC--TAGC
```

One of skill in the art will appreciate that there are exact and approximate algorithms for sequence alignment. Exact algorithms will find the highest scoring alignment, but can be computationally expensive. The two most well-known exact algorithms are Needleman-Wunsch (*J Mol Biol*, 48(3): 443-453, 1970) and Smith-Waterman (*J Mol Biol*, 147(1): 195-197, 1981; *Adv. in Math.* 20(3), 367-387, 1976). A further improvement to Smith-Waterman by Gotoh (*J Mol Biol*, 162(3), 705-708, 1982) reduces the calculation time from $O(m^2n)$ to $O(mn)$ where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon.com's cloud computing resources available at http://aws.amazon.com. All of the above journal articles are incorporated herein by reference in their entireties.

The Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The SW algorithm is easily expressed for an n×n matrix H, representing the two strings of length n and in, in terms of equation (1) below:

$$H_{k0}=H_{0l}=0 \text{ (for } 0 \leq k \leq n \text{ and } 0 \leq l \leq m) \quad (1)$$

$$H_{ij}=\max\{H_{i-1,j-1}+s(a_i,b_j), H_{i-1,j}-W_{in}, H_{i,j-1}-W_{del}, 0\}$$
$$\text{(for } 1 \leq i \leq n \text{ and } 1 \leq j \leq m)$$

In the equations above, $s(a_i,b_j)$ represents either a match bonus (when $a_i=b_j$) or a mismatch penalty (when $a_i \neq b_j$), and insertions and deletions are given the penalties $W_{in}$ and $W_{del}$, respectively. In most instance, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values ($H_{i-1,j-1}$, $H_{i-1,j}$, or $H_{i,j-1}$) was used to compute the final maximum value for each cell. The backtracking stops when a zero is reached. See, e.g., FIG. 3B, which does not represent the prior art, but illustrates the concept of a backtrack, and the corresponding local alignment when the backtrack is read. Accordingly, the "best alignment," as determined by the algorithm, may contain more than the minimum possible number of insertions and deletions, but will contain far less than the maximum possible number of substitutions.

When applied as SW or SW-Gotoh, the techniques use a dynamic programming algorithm to perform local sequence alignment of the two strings, S and A, of sizes m and n, respectively. This dynamic programming technique employs tables or matrices to preserve match scores and avoid recomputation for successive cells. Each element of the string can be indexed with respect to a letter of the sequence, that is, if S is the string ATCGAA, S[1]=A, S[4]=G, etc. Instead of representing the optimum alignment as $H_{i,j}$ (above), the optimum alignment can be represented as B[j,k] in equation (2) below:

$$B[j,k]=\max(p[j,k],i[j,k]d[j,k],0) \text{ (for } 0<j\leq m, 0<k\leq n) \quad (2)$$

The arguments of the maximum function. B[j,k], are outlined in equations (3)-(5) below, wherein MISMATCH_PENALTY, MATCH_BONUS, INSERTION_PENALTY, DELETION_PENALTY, and OPENING_PENALTY are all constants, and all negative except for MATCH_BONUS. The match argument, p[j,k], is given by equation (3), below:

$$p[j,k] = \max(p[j-1,k-1], i[j-1,k-1], d[j-1,k-1]) + \quad (3)$$
$$\text{MISMATCH\_PENALTY, if } S[j] \neq A[k]$$
$$= \max(p[j-1,k-1], i[j-1,k-1], d[j-1,k-1]) +$$
$$\text{MATCH\_BONUS, if } S[j] = A[k]$$

the insertion argument i[j,k], is given by equation (4), below:

$$i[j,k]=\max(p[j-1,k]+\text{OPENING\_PENALTY}, i[j-1,k],$$
$$d[j-1,k]+\text{OPENING\_PENALTY})+$$
$$\text{INSERTION\_PENALTY} \quad (4)$$

and the deletion argument d[j,k], is given by equation (5), below:

$$d[j,k]=\max(p[j,k-1]+\text{OPENING\_PENALTY}, i[j,k-1]+$$
$$\text{OPENING\_PENALTY}, d[j,k-1])+\text{DELETION\_}$$
$$\text{PENALTY} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. *Curr Top Comp Mol Biol.* Cambridge, Mass.: The MIT Press, 2002) for DNA would be:
MATCH_BONUS: 10
MISMATCH_PENALTY: −20
INSERTIONYENALTY: −40
OPENING_PENALTY: −10
DELETION_PENALTY: −5

The relationship between the gap penalties (INSERTION_PENALTY, OPENING_PENALTY) above help limit the number of gap openings, i.e., favor grouping gaps together, by setting the gap insertion penalty higher than the gap opening cost. Of course, alternative relationships between MISMATCH_PENALTY, MATCH_BONUS, INSERTION_PENALTY. OPENING_PENALTY and DELETION_PENALTY are possible.

Once the alignment is complete, the aligned sequences can be assembled to produce a sequence that can be compared to a reference (i.e., a genetic standard) to identify variants. The variants can provide insight regarding diseases, stages of disease, recurrence and the like. In the case of amino acid alignments, the assembled amino acid sequences can be compared to a standard to determine evolutionary information about the protein, or functional information about the protein.

A limitation of state-of-the-art alignment methods, e.g., Smith-Waterman, is that the alignment algorithms have difficulty aligning smaller reads, e.g., between 20 and 1000 base pairs (bp) in the presence of structural variations that are larger than or of similar size to the read. Structural variations are typically large sequence deviations, e.g., 100 bp or more, e.g., typically between 1 kilobase and 3 megabases in length. Structural variants can include duplications, inversions, translocations or genomic imbalances (insertions and deletions), and by definition they span more than several base pairs. Commonly known structural variations include copy-number variants whereby an abnormal number of copies of a specific genomic area are duplicated in a region of a chromosome. Such variations have been linked to cancer as well as autoimmune and neurological disorders.

When shorter reads, representing a portion of a sequence containing a structural variation, are aligned to a reference sequence using state-of-the-art techniques, the reads are often discarded as errant because the alignment scores of the reads against the reference are below a threshold for meaningful reads, since the structural variation isn't present in the reference. In other instances, the reads align, but the specific sequence of the read is discounted because the alignment score is low enough (and the aligned sequence is thus presumed to be "noisy" enough) that it is unclear whether a particular base in the sequence is a result of a mutation in the structural variation or just a misread of the "normal" structural variation.

An additional problem is presented when a mutation or variant, e.g., a small indel or polymorphism, is located in the read in close proximity to a structural variation. The difficulty of aligning the structural variation may cause reads containing both the mutation and the structural variation to be discarded as "unalignable." The more such reads are discarded, the more likely it becomes that the mutation gets missed entirely. As a result, meaningful rare variants or mutations (used interchangeably here) close to structural variations can be rejected due to the low alignment score associated with the structural variation. These overlooked variants may have (undiscovered) roles in regulating disease.

Because failing to detect rare variants in proximity to structural variations significantly limits the quality of genetic analysis, there is a need for sequence alignment techniques that can account for structural variations, resulting in better alignment of rare mutations or variants.

SUMMARY

The invention generally provides algorithms and methods for their implementation that transform linear, local sequence alignment processes such as, for example, Smith-Waterman-Gotoh, into multi-dimensional alignment algorithms that provide increased parallelization, increased speed, increased accuracy, and the ability to align reads through an entire genome. In certain aspects, the invention is implemented on assembled reference constructs that can account for the variability in genetic sequences within a species, population, or even among different cells in a single organism. A Particular benefit of reference constructs and alignment algorithms of the invention is the ability to align sequence reads that match to different sequences at a certain position of a reference sequence. That is, a reference construct allows a sequence read to align against one of at least two different sequence paths at a certain position—e.g., a path that follows a sequence common to a reference sequence or another path that follows sequence uncommon to that reference sequence (e.g. mutations, polymorphisms, structural variants).

Algorithms of the invention provide for a "look-back" type analysis of sequence information (as in Smith-Waterman), however, in contrast to known linear methods, the look back of the invention is conducted through a multi-dimensional space that includes multiple pathways and multiple nodes in order to provide more accurate alignment of complex and lengthy sequence reads, while achieving lower overall rates of mismatches, deletions, and insertions.

In practice, the invention is implemented by aligning sequence reads to a series of directed, acyclic sequences spanning branch points that account for all, or nearly-all, of the possible sequence variation in the alignment, including insertions, deletions, and substitutions. Such constructs, often represented as directed acyclic graphs (DAGs) can be easily assembled from available sequence databases, including "accepted" reference sequences and variant call format (VCF) entries. When combined with DAGs, or other constructs that take into account known variation, the disclosed algorithm thus provides a multi-dimensional approach to sequence alignment that greatly improves alignment accuracy and allows for sequence resolution not possible with conventional algorithms. The techniques can be used with any sequence information, in fact, however they are most useful for aligning nucleic acid sequences and amino acid sequences, as discussed herein.

The invention additionally provides methods to make specific base calls at specific loci using a reference sequence construct, e.g., a DAG that represents known variants at each locus of the genome. Because the sequence reads are aligned to the DAG during alignment, the subsequent step of comparing a mutation, vis-h-vis the reference genome, to a table of known mutations can be eliminated. Using the disclosed methods, it is merely a matter of identifying a nucleic acid read as being located at a known mutation represented on the DAG and calling that mutation. Alternatively, when a mutation is not known (i.e., not represented in the reference sequence construct), an alignment will be found and the variant identified as a new mutation. The method also makes it possible to associate additional information, such as specific disease risk or disease progression, with known mutations that are incorporated into the reference sequence construct. Furthermore, in addition to having the potential to find all genetically relevant results during alignment, the disclosed methods reduce the computational resources required to make the alignments while allowing for simultaneous comparison to multiple reference sequences.

The invention additionally includes methods for constructing a directed acyclic graph data structure (DAG) that represents known variants at positions within the sequence of an organism. The DAG may include multiple sequences at thousands of positions, and may include multiple variants at each position, including deletions, insertions, translations, inversions, and single-nucleotide polymorphisms (SNPs). It is also possible to tag each variant in the DAG with correlated diagnostic information, such as "breast cancer," thereby reducing the steps needed to identify the risks to a patient providing a sample. In some embodiments, the variants will be scored, weighted, or correlated with other variants to reflect the prevalence of that variant as a marker for disease.

The invention additionally includes systems for executing methods of the invention. In one embodiment, a system comprises a distributed network of processors and storage capable of comparing a plurality of sequences (i.e., nucleic acid sequences, amino acid sequences) to a reference sequence construct (e.g., a DAG) representing observed variation in a genome or a region of a genome. The system is additionally capable of aligning the nucleic acid reads to produce a continuous sequence using an efficient alignment algorithm. Because the reference sequence construct compresses a great deal of redundant information, and because the alignment algorithm is so efficient, the reads can be tagged and assembled on an entire genome using commercially-available resources. The system comprises a plurality of processors that simultaneously execute a plurality of comparisons between a plurality of reads and the reference sequence construct. The comparison data may be accumulated and provided to a health care provider. Because the comparisons are computationally tractable, analyzing sequence reads will no longer represent a bottleneck between NGS sequencing and a meaningful discussion of a patient's genetic risks.

According to certain aspects, the invention provides methods and systems for aligning a nucleic acid sequence to a reference sequence construct that accounts for different structural variations within a sequence to be aligned. With the structural variations represented in the reference sequence construct, sequence reads which include part of the structural variation are aligned to the reference sequence with a higher alignment score than possible with linear reference sequences that do not account for the variation. As a result, the different paths of the reference construct advantageously allow sequence reads containing large known sequence variations or portions thereof to successfully align to the construct for subsequent analysis. With a structural variant of a sequence read properly aligned, other sequence data that are part of the sequence read, especially those in close proximity to the structural variant likewise align to the reference construct with a higher alignment score than possible with linear reference sequence.

The consistent, reliable alignment of reads containing a structural variant allows capture of sequence data that otherwise might be discarded as unaligned sequence. Because of this, algorithms and reference constructs of the invention are used to capture rare variants located in proximity to a structural variation. A rare variant is one that occurs in the sample or population at a frequency of less than about 5% and preferably less than about 1%. For the purposes of the invention, rare variants may also include "unrepresented" variants, i.e., variants that are not reflected in the reference being used, be it a linear reference sequence (in pre-existing methods) or the reference constructs of the invention. For example, a rare variant that is close to a structural variant (such that a sequence read includes at least portions of the structural variant and the rare variant) will align to a reference construct of the invention along with the structural variant. As a direct result of the structural variant's alignment, the rare variant close to the structural variant will be present in a large number of otherwise well-aligned and reliable reads because of the proper alignment of the structural variant in the sequence read to the reference construct. The consistent presence of the rare variant causes it to be recognized as a legitimate genetic variant rather than sequencing error. The use of a multi-path alignment approach as described herein allows resolution of rare sequence variations that would likely be lost using a linear reference alignment approach.

BRIEF DESCRIPTION OF THE FIGURES

FIG. 1A shows the starting reference sequence and the addition of a deletion. FIG. 1B shows the addition of an insertion and a SNP, thus arriving at the Final DAG used for alignment;

FIG. 6A shows three nucleic acid sequences that illustrate a rare variant in the presence of a structural variation, as well as a read that overlaps with a sequence having both a structural variation and a rare variant (S**);

FIG. 6B illustrates a lack of overlap between a read that overlaps with a sequence having both a structural variation and a rare variant (S**), and the "accepted" reference sequence (S);

FIG. 6C illustrates a DAG incorporating two of the three sequences from FIG. 6A;

FIG. 6D illustrates alignment of the read to the DAG incorporating two of the three sequences from FIG. 6A;

DETAILED DESCRIPTION

Figure 1A:
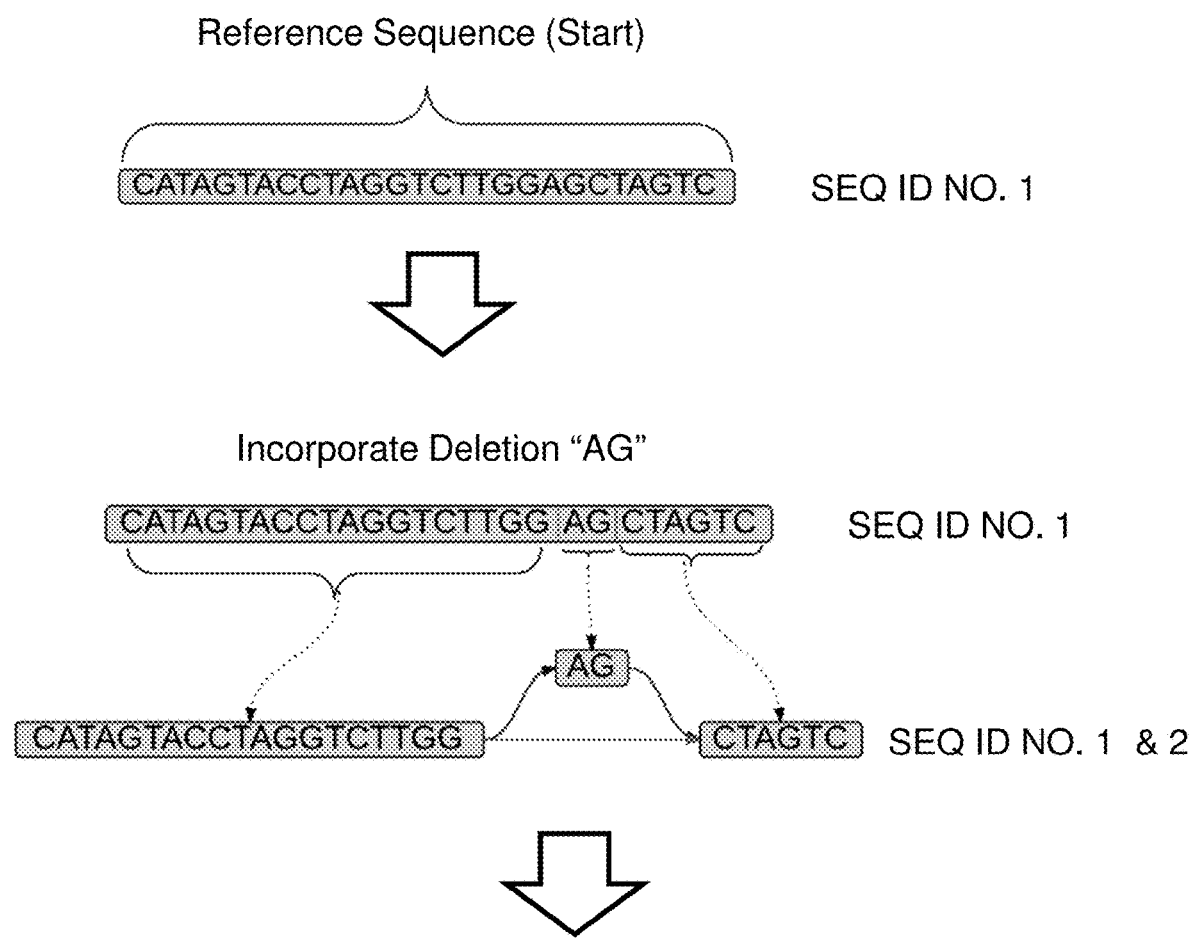
FIGS. 1A and 1B depict the construction of a directed acyclic graph (DAG) representing genetic variation in a reference sequence.

The invention provides methods for identifying rare variants near a structural variation in a genetic sequence, for example, in a nucleic acid sample taken from a subject. The invention additionally includes methods for aligning reads (e.g., nucleic acid reads) to a reference sequence construct accounting for the structural variation, methods for building a reference sequence construct accounting for the structural variation or the structural variation and the rare variant, and systems that use the alignment methods to identify rare variants. The method is scalable, and can be used to align millions of reads to a construct thousands of bases long, or longer.

The invention also includes methods for aligning sequences (e.g., nucleic acid sequences, amino acid sequences) to a reference sequence construct, methods for building the reference sequence construct, and systems that use the alignment methods and constructs to produce alignments and assemblies. The reference sequence construct may be a directed acyclic graph (DAG), as described below, however the reference sequence can be any representation reflecting genetic variability in the sequences of different organisms within a species, provided the construct is formatted for alignment. The genetic variability may also be between different tissues or cells within an organism. In general, the reference sequence construct will comprise portions that are identical and portions that vary between sampled sequences. Accordingly, the constructs can be thought of as having positions (i.e., according to some canonical ordering) that comprise the same sequence(s) and some positions that comprise alternative sequences, reflecting genetic variability. The application additionally discloses methods for identifying a disease or a genotype based upon alignment of a nucleic acid read to a location in the construct. The methods are broadly applicable to the fields of genetic sequencing and mutation screening.

Reference Sequence Constructs

Unlike prior art sequence alignment methods that use a single reference sequence to align and genotype nucleic acid reads, the invention uses a construct that can account for the variability in genetic sequences within a species, population, or even among different cells in a single organism. Representations of the genetic variation can be presented as directed acyclic graphs (DAGs) (discussed above) row-column alignment matrices, or deBruijn graphs, and these constructs can be used with the alignment methods of the invention provided that the parameters of the alignment algorithms are set properly (discussed below).

In preferred embodiments of the invention, the construct is a directed acyclic graph (DAG), i.e., having a direction and having no cyclic paths. (That is, a sequence path cannot travel through a position on the reference construct more than once.) In the DAG, genetic variation in a sequence is represented as alternate nodes. The nodes can be a section of conserved sequence, or a gene, or simply a nucleic acid. The different possible paths through the construct represent known genetic variation. A DAG may be constructed for an entire genome of an organism, or the DAG may be constructed only for a portion of the genome, e.g., a chromosome, or smaller segment of genetic information. In some embodiments, the DAG represents greater than 1000 nucleic acids, e.g., greater than 10,000 nucleic acids, e.g., greater than 100,000 nucleic acids, e.g., greater than 1,000,000 nucleic acids. A DAG may represent a species (e.g., *Homo sapiens*) or a selected population (e.g., women having breast cancer), or even smaller subpopulations, such as genetic variation among different tumor cells in the same individual.

A simple example of DAG construction is shown in FIG. 1A. As shown in FIG. 1A, the DAG begins with a reference sequence, shown in FIG. 1A as SEQ ID NO. 1: CATAGTACCTAGGTCTTGGAGCTAGTC. In practice, the reference sequence is often much longer, and may be an entire genome. The sequence is typically stored as a FASTA or FASTQ file. (FASTQ has become the default format for sequence data produced from next generation sequencers). In some embodiments, the reference sequence may be a standard reference, such as GRCh37. As recognized by those of skill, each letter (or symbol) in the sequence actually corresponds to a nucleotide (e.g., a deoxyribonucleotide or a ribonucleotide) or an amino acid (e.g., histidine, leucine, lysine, etc.).

At the next step, a variant is added to the reference sequence, as shown in the bottom image of FIG. 1A. As shown in FIG. 1A the variant is the deletion of the sequence "AG" from the reference between the lines in the figure, i.e., SEQ ID NO. 2. Graphically, this deletion is represented by breaking the reference sequence into nodes before and after the deletion, and inserting two strings between the nodes. The different paths create alternative sequences within the reference construct. One of the paths represents a sequence common to the reference sequence, and one of the paths represents a sequence uncommon to the reference sequence. In FIG. 1A, one path between the nodes represents the sequence common to the reference sequence, while the other path represents the deletion uncommon to the reference sequence. In practice, the variants are called to the DAG by applying the entries in a variant call format (VCF) file, such as can be found at the 1000 Genomes Project website. Because each VCF file is keyed to a specific reference genome, it is not difficult to identify where the strings should be located. In fact, each entry in a VCF file can be thought of as combining with the reference to create separate graph, as displayed in FIG. 2. Note the VCF entries in FIG. 2 do not correspond to the VCF entries of FIG. 1.

Figure 1B:
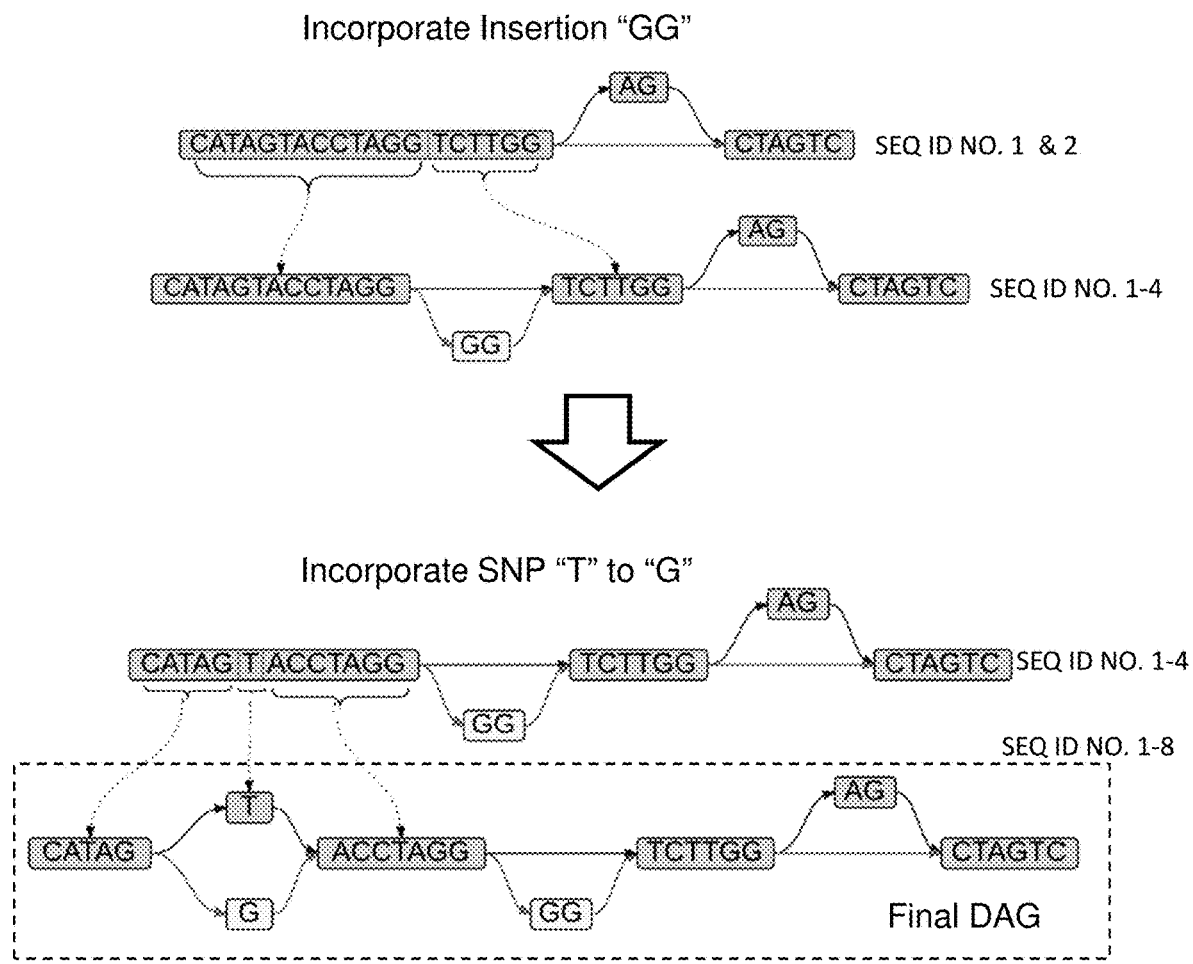
Figure 2:
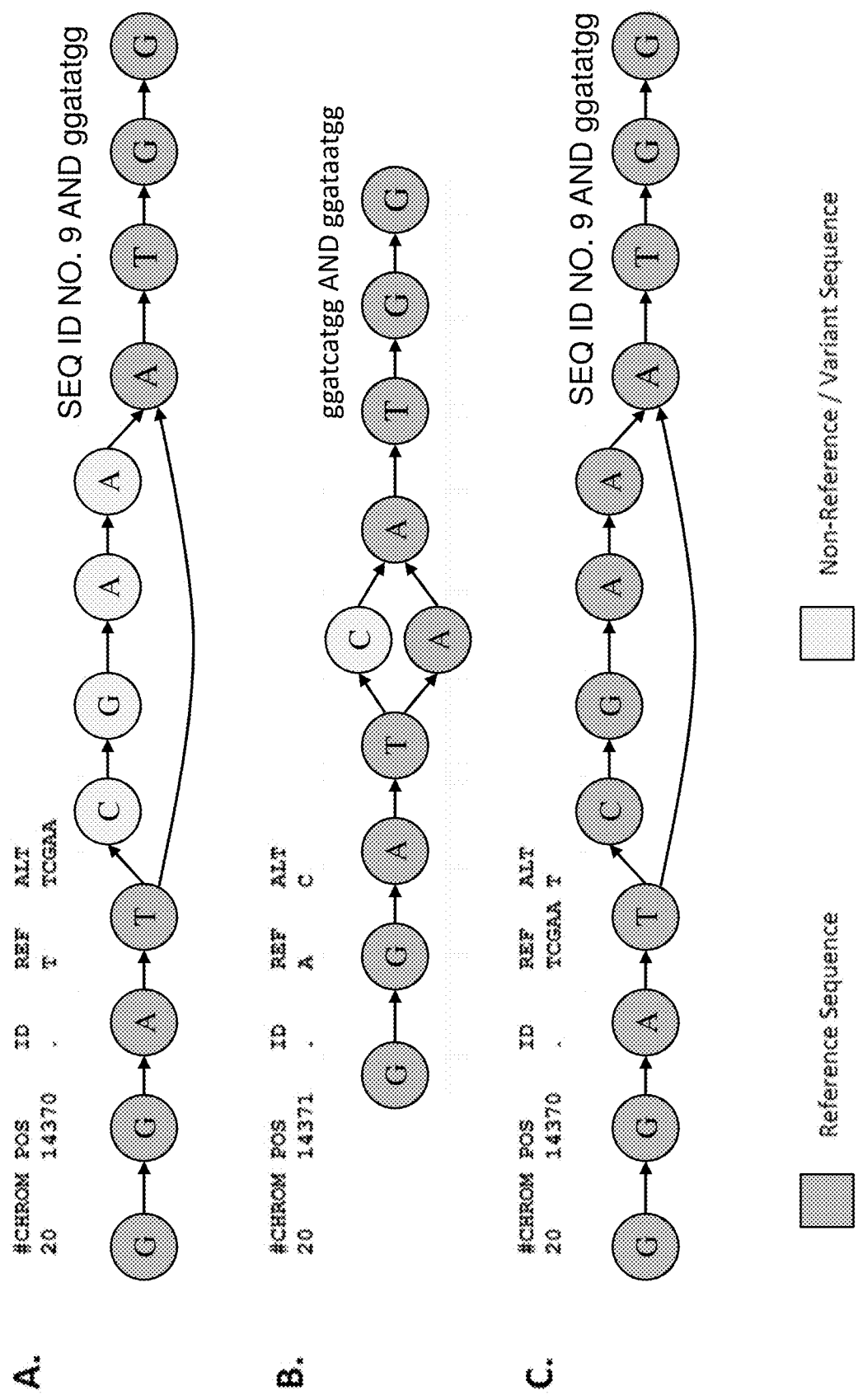
FIG. 2 depicts three variant call format (VCF) entries represented as directed acyclic graphs.

Moving to FIG. 1B, a second VCF entry, corresponding to an insertion "GG" at a specific position is added to produce an expanded DAG, i.e., including SEQ ID NO. 3 and SEQ ID NO. 4. Next, a third VCF entry can be added to the expanded DAG to account for a SNP earlier in the reference sequence, i.e., including SEQ ID NOS. 5-8. Thus, in three steps, a DAG has been created against which nucleic acid reads can be aligned (as discussed below.)

In DAG reference constructs, the sequence paths (common and uncommon sequences to a reference) are both considered variants within the reference construct because they represent the alternative sequences that may be included in a subject's sequence.

In practice, the DAGs are represented in computer memory (hard disk, FLASH, cloud memory, etc.) as a set of nodes, S, wherein each node is defined by a string, a set of parent nodes, and a position. The string is the node's "content," i.e., sequence; the parent nodes define the node's position with respect to the other nodes in the graph; and the position of the node is relative to some canonical ordering in the system, e.g., the reference genome. While it is not strictly necessary to define the graph with respect to a reference sequence, it does make manipulation of the output data simpler. Of course, a further constraint on S is that it cannot include loops.

Extrapolating this DAG method to larger structures, it is possible to construct DAGs that incorporate thousands of VCF entries representing the known variation in genetic sequences for a given region of a reference. Nonetheless, as a DAG becomes bulkier, the computations do take longer, and for many applications a smaller DAG is used that may only represent a portion of the sequence, e.g., a chromosome. In other embodiments, a DAG may be made smaller by reducing the size of the population that is covered by the DAG, for instance going from a DAG representing variation in breast cancer to a DAG representing variation in triple negative breast cancer. Alternatively, longer DAGs can be used that are customized based upon easily identified genetic markers that will typically result in a large portion of the DAG being consistent between samples. For example, aligning a set of nucleic acid reads from an African-ancestry female will be quicker against a DAG created with VCF entries from women of African ancestry as compared to a DAG accounting for all variations known in humans over the same sequence. It is to be recognized that the DAGs of the invention are dynamic constructs in that they can be modified over time to incorporate newly identified mutations. Additionally, algorithms in which the alignment results are recursively added to the DAG are also possible.

In the instance of string-to-DAG alignment, the gap penalties can be adjusted to make gap insertions even more costly, thus favoring an alignment to a sequence rather than opening a new gap in the overall sequence. Of course, with improvements in the DAG (discussed above) the incidence of gaps should decrease even further because mutations are accounted for in the DAG.

Alignment Algorithm

In one embodiment, an algorithm is used to align sequence reads against a directed acyclic graph (DAG). In contrast to the algorithm expressed in the Background, the alignment algorithm identifies the maximum value for Ce by identifying the maximum score with respect to each sequence contained at a position on the DAG (e.g., the reference sequence construct). In fact, by looking "backwards" at the preceding positions, it is possible to identify the optimum alignment across a plurality of possible paths.

The algorithm of the invention is carried out on a read (a.k.a. "string") and a directed acyclic graph (DAG), discussed above. For the purpose of defining the algorithm, let S be the string being aligned, and let D be the directed acyclic graph to which S is being aligned. The elements of the string, S, are bracketed with indices beginning at 1. Thus, if S is the string ATCGAA, $S[1]=A$, $S[4]=G$, etc.

For the DAG, each letter of the sequence of a node will be represented as a separate element, d. A predecessor of d is defined as:

(i) If d is not the first letter of the sequence of its node, the letter preceding d in its node is its (only) predecessor;

(ii) If d is the first letter of the sequence of its node, the last letter of the sequence of any node that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding $H_{i,j}$ in equation 1 in the Background section. Specifically, determining M[j,d] involves finding the maximum of a, i, e, and 0, as defined below:

$$M[j,d] = \max\{a, i, e, 0\} \quad (6)$$

where
e=max{M[j,p*]+DELETE PENALTY} for p* in P[d]
i=M[j−1,d]+INSERT_PENALTY
a=max{M[j−1,p*]+MATCH_SCORE} for p* in P[d], if S[j]=d;
max{M[j−1, p*]+MISMATCH_PENALTY} for p* in P[d], if S[j]≠d As described above, e is the highest of the alignments of the first j characters of S with the portions of the DAG up to, but not including, d, plus an additional DELETE_PENALTY. Accordingly, if d is not the first letter of the sequence of the node, then there is only one predecessor, p, and the alignment score of the first j characters of S with the DAG (up-to-and-including p) is equivalent to M[j,p]+DELETE_PENALTY. In the instance where d is the first letter of the sequence of its node, there can be multiple possible predecessors, and because the DELETE_PENALTY is constant, maximizing [M[j,p*]+DELETE_PENALTY] is the same as choosing the predecessor with the highest alignment score with the first j characters of S.

In equation (6), i is the alignment of the first j−1 characters of the string S with the DAG up-to-and-including d, plus an INSERT_PENALTY, which is similar to the definition of the insertion argument in SW (see equation 1).

Additionally, a is the highest of the alignments of the first j characters of S with the portions of the DAG up to, but not including d, plus either a MATCH-SCORE (if the jth character of S is the same as the character d) or a MISMATCH_PENALTY (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PENALTY or MATCH_SCORE added, depending upon whether d and the jth character of S match. In the instance where d is the first letter of the sequence of its node, there can be multiple possible predecessors. In this case, maximizing {M[j, p*]+MISMATCH_PENALTY or MATCH_SCORE} is the same as choosing the predecessor with the highest alignment score with the first j−1 characters of S (i.e., the highest of the candidate M[j−1,p*] arguments) and adding either a MISMATCH_PENALTY or a MATCH_SCORE depending on whether d and the jth character of S match.

Again, as in the SW algorithm discussed in the Background, the penalties, e.g., DELETE_PENALTY, INSERT_PENALTY, MATCH_SCORE and MISMATCH_PENALTY, can be adjusted to encourage alignment with fewer gaps, etc.

As described in the equations above, the algorithm finds the maximum value for each read by calculating not only the insertion, deletion, and match scores for that element, but looking backward (against the direction of the DAG) to any prior nodes on the DAG to find a maximum score. Thus, the algorithm is able to traverse the different paths through the DAG, which contain the known mutations. Because the graphs are directed, the backtracks, which move against the direction of the graph, follow the preferred variant sequence toward the origin of the graph, and the maximum alignment score identifies the most likely alignment within a high degree of certainty. While the equations above are represented as "maximum" values. "maximum" is intended to cover any form of optimization, including, for example, switching the signs on all of the equations and solving for a minimum value.

Figure 3A:
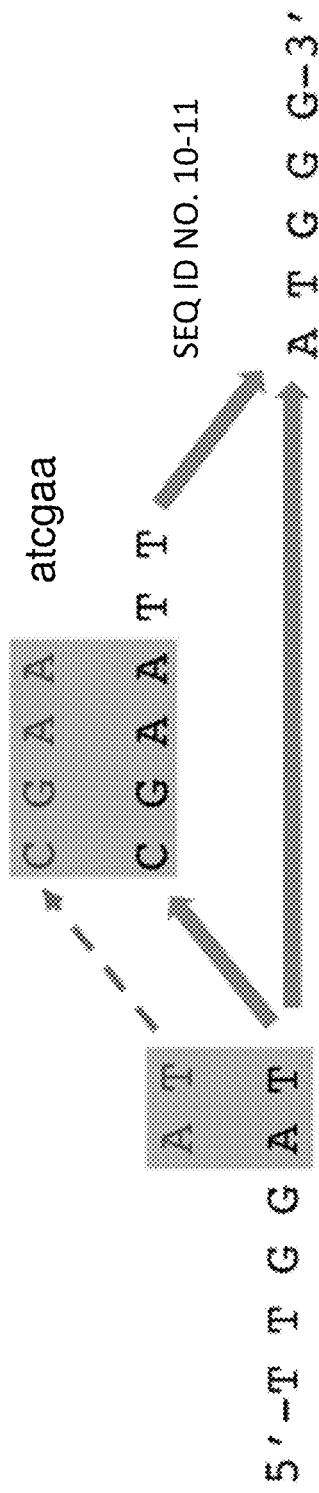
FIG. 3A shows a pictorial representation of aligning a nucleic acid sequence read against a construct that accounts for an insertion event as well as the reference sequence.
Figure 3B:
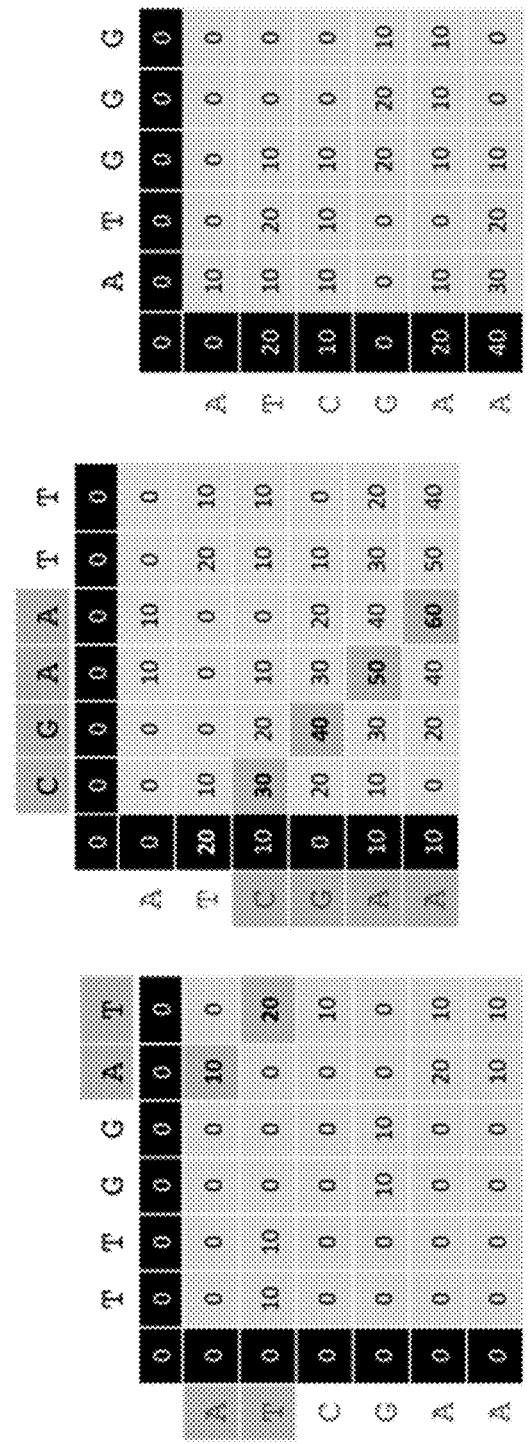
FIG. 3B shows the matrices and the backtrack used to identify the proper location of the nucleic acid sequence read "ATCGAA"

Implementation of the disclosed algorithm is exemplified in FIG. 3A, where a sequence "ATCGAA" is aligned against a DAG that represents a reference sequence SEQ ID NO. 10: TTGGATATGGG and a known insertion event SEQ ID NO. 11: TTGGAT CGAATT ATGGG, where the insertion is underlined. FIG. 3A shows a pictorial representation of the read being compared to the DAG while FIG. 3B shows the actual matrices that correspond to the comparison, like the Smith-Waterman technique discussed in the Background, the algorithm of the invention identifies the highest score and performs a backtrack to identify the proper location of the read. FIGS. 3A and B also highlights that the invention produces an actual match for the string against the construct, whereas the known methods (e.g., SW) would have been more likely to align the string to the wrong part of the reference, or reject the string as not generating a sufficiently-high alignment score to be included in the alignment. In the instances where the sequence reads include variants that were not included in the DAG, the aligned sequence will be reported out with a gap, insertion, etc.

Applications of the Reference Sequence Construct

One benefit of the reference construct and alignment algorithm of the invention is its ability to align sequence reads to either a first sequence or a second sequence at a certain position of the reference sequence construct. That is, a reference sequence construct of the invention allows a sequence read to align against one of at least two different sequence paths at a certain position—e.g., a path that follows a sequence equivalent to a reference sequence and another path that follows a known sequence equivalent to the reference sequence including variants (e.g. mutations, polymorphisms, copy number variations). Thus, known variations in sequences can be reliably accounted for and identified using techniques of the invention by aligning reads containing the known variation to a sequence path that includes that variation.

A variation (also referred to as variant) may include either one of the two or more alternative sequences (i.e., when different sequences form two or more paths) at a certain position in the reference sequence construct. In another sense, because the reference sequence construct incorporates sequencing data associated with several reference populations/data sets, any alternative sequence within the DAG construct is considered a variant. A reference sequence of the construct is any sequence used as a baseline for the DAG and is typical a long sequence used for analysis, and may be portion of, or an entire genome. The reference sequence may be a sequence common to a certain species (e.g. *Homo sapiens*) or may be common to certain patient populations (e.g. cancer patients).

In certain embodiments, a variant may be considered a common sequence or an uncommon sequence to the reference sequence. As discussed herein, a common sequence variant is any sequence path in the reference construct that follows the reference sequence chosen as the baseline. As such, whether a sequence variation is "common" or "uncommon" to the reference sequence depends on what is chosen for the baseline reference sequence. For example, a reference construct at a certain position may include a first sequence path common to normal, healthy individuals and a second sequence path with a mutation common to individuals with breast cancer. If the baseline reference is a reference sequence common to breast cancer patients, then the first sequence path directed to normal healthy individuals is an uncommon variant, and the second sequence path for breast cancer individuals is a common variant. If the baseline reference is considered a reference sequence common to normal, healthy individuals, then the first sequence path directed to normal, healthy individuals is a common variant, and the second sequence path directed to breast cancer patients is an uncommon variant.

The different paths of the reference construct advantageously allow sequence reads with large known sequence deviations to successfully align to the construct for subsequent analysis, whereas traditional one-dimensional reference sequences reject such large deviations due to a low alignment score. Large known sequence variations, often referred to as structural variants, are typically between 1 Kb to 3 Mb in size. However, for purposes of this application, structural variants may include any large sequence variant within a sequence read that because of its size prevents the sequence read from aligning to a linear reference sequence or aligns very poorly (e.g. low alignment score) to a reference sequence. In certain embodiments, the sequence length of the structural variant is about 100 bp, 200, bp, 300 bp, 400 bp, 500 bp, 600 bp, 700 bp, 800, bp, 1 Kb, 1.1. Kb, 1.2 Kb, 1.3 Kb, 1.4 Kb, 1.5 Kb, 1.6 Kb, 1.7 Kb, 1.8 Kb, 1.9 Kb, 2.0 Kb . . . 2.0 Mb, 2.1 Mb, 2.2 Mb, 2.3 Mb, 2.4 Mb, 2.5 Mb, 2.6 Mb, 2.7 Mb, 2.8 Mb, 2.9 Mb, 3.0 Mb, etc. Structural variations provide important insight into a subject as they contribute to genetic diversity and disease susceptibility.

Unlike the current invention, traditional alignment methods (e.g. linear reference sequences) are unlikely to identify structural variations, and even less likely to identify rare variants located near a structural variation. Rare variants include any mutations (such as indel or polymorphism) that are found in a low-probably in a given population. For example, a rare variant may have a minor allele frequency ranging from, for example, 25% or fewer; 20% or fewer; 15% or fewer; 10% or fewer; or 5% or fewer. (Minor allele frequency (MAF) refers to the frequency at which the least common allele occurs in a given population.) In some instances, rare variants include variants that have not yet been identified, i.e., the variants aren't represented in the reference to which the read is aligned. In some instances the rare variant has not been cataloged in a VCF file. From the perspective of the alignment mechanism, such variants are effectively never-before-seen regardless of their actual frequency in a population of samples. A rare variant located near a structural variant may be separated from the structural variant by about the length of the read, i.e., about 100 bp or fewer. The invention is not limited to this spacing however. In some instances, a rare variant located near a structural variant has a separation between the rare variant and the structural variant may range from about 1 bp to about 1 Mbp, e.g., about 10 bp to about 10,000 bp, e.g., about 100 bp to about 1000 bp.

Traditional alignment methods fail to recognize rare variants near structural variants because of the combination of two factors. First, traditional alignment methods align the subject's reads to single linear reference sequences that do not take into account the structural variation, even if it is known. Second, almost all reads containing the rare variant will also contain the structural variant. As the base separation between the rare variant and the structural variant decreases, more reads containing the rare variant will also contain the structural variant. These two factors significantly increase the chance that sequence reads containing both the structural variant and the rare variant will fail to align. Since the structural variant is large and not reflected in the reference sequence, reads that overlap with it will be rejected by alignment algorithms as "unalignable" (i.e., too different from the reference to match any part of it). In that case, both the structural variant and the rare variant are discarded. The lack of a match between a read with a structural variant and rare variant and the corresponding, "proper" genomic location of the read on the linear reference sequence may result in alignment of the read to an incorrect location on the genome. Even if the read or portion thereof is aligned to the right general location, the matching algorithm will likely drop the rare mutation in trying to achieve an acceptable alignment. This is especially likely when the variant is not represented in the reference to which the reads are being aligned. Any reads that manage to align correctly and contain the rare variant will be treated as less reliable due to poor alignment quality and the low number of alignments, both of which suggest that the alignment is merely random error. While the large known structural variant may still be called despite the poor read reliability because it is known, the rare variant is usually classified as noise/error compared to the known structural variant and discarded.

Because rare variants are generally accepted to confer a substantial risk of disease, it is of critical importance maximize one's ability to detect rare variants during sequence assembly. The reference constructs of the invention minimize nonalignment of structural variants and rare variants during the alignment process because references constructs of the invention can account for any known structural variants. By including at least two structural variants at a certain location in the reference construct, the invention allows for sequence reads that include a portion of at least one of the structural variants to align to the reference construct. That is, sequence reads that include a portion of a known structural variant are aligned and accounted for, whereas the same structural variant would fail to align in a linear reference structure. The result of the invention is that reads that include structural variants are able to properly align to the DAG with a high degree of reliability and accuracy because the reads are treated as matches rather than mismatches.

With the structural variant properly aligned, other sequence data that is part of the sequence read with the structural variant likewise aligns to the reference construct. For example, a rare variant that is close to a structural variant (such that a sequence read includes at least portions of the structural variant and the rare variant) will align to the reference construct along with the structural variant. Thus, a rare variant next to a structural variant will present in a large number of otherwise well-aligned and reliable reads because of the proper alignment of the structural variant in the sequence read to the DAG reference construct. The consistent presence of the rare variant causes it to be recognized as a legitimate genetic variant rather than sequencing error, even if the variant is not represented in the reference construct.

FIGS. 6A-6F exemplify use of reference constructs of the invention to identify rare variants near structural variants.

Figure 6E:
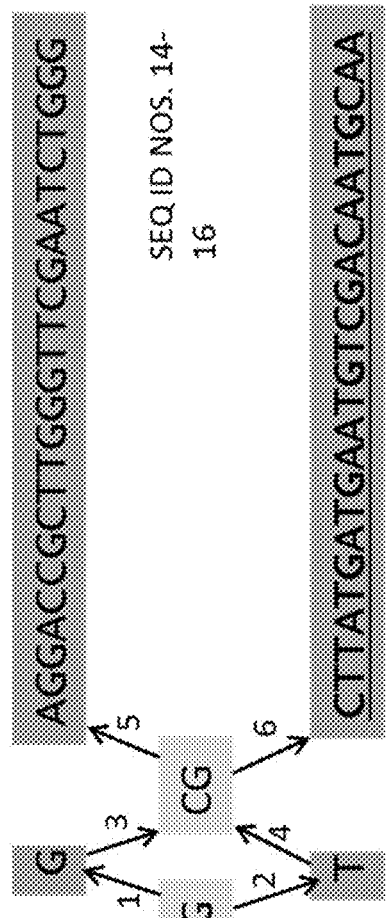
FIG. 6E illustrates a DAG incorporating all three of the sequences from FIG. 6A.

FIG. 6A outlines three hypothetical sequences, each 50 nucleotides in length: Reference Sequence S (SEQ ID NO. 14), Sequence S* with structural variation (SEQ ID NO. 15), and Sequence S** with structural variation and rare variant (SEQ ID NO. 16). Sequence S* and Sequence S include a known structural variation to the Reference Sequence S that spans from the 26th position to the 50th position. In practice, structural variations are typically 100 bp or greater. The length of the structural variation shown in FIGS. 6A-6F is for illustrative purposes. As shown throughout FIGS. 6A-6F, the known structural variation is bolded and highlighted. Sequence S also includes a rare variant to the Reference Sequence S, which is a substitution mutation where T replaces the G at position 23. FIG. 6A also shows a sequence read (referred to as Read 1) of Sequence S** spanning from the 20th position to the 34th position. Accordingly, Read 1 includes a portion of the structural variant (from the 26th position to the 34th) and the rare variant at the 23rd position. In practice, the sequence read and the structural variation are likely longer than illustrated in FIG. 6. Additionally, the rare variant may be further from the structural variation.

FIG. 6B illustrates alignment of Read 1 of Sequence S to the Reference Sequence S. Particularly, FIG. 6B illustrates the inability to align Read 1 of Sequence S to the Reference Sequence S in the traditional linear form. When aligned linearly, the majority of the nucleotides in Read 1 differ from the Reference Sequence from position 20 to position 34. Despite the mismatches, Read 1 will ideally align to the Reference Sequence from position 20 to position 34 in order to appropriately reveal the rare and structural sequence variations. However, due to the high level of mismatch, algorithms such as Smith-Waterman or Needleman-Wunsch are not likely to assign a score to Read 1 that would satisfy quality thresholds used in practice required for alignment. As a result, Read 1 would fail to align to the linear Reference Sequence from position 20 to position 34, and the data from Read 1 will be rejected. In addition, if the Reference Sequence spans a genome (many orders of magnitude above the 50 nucleotides shown), Read 1 is likely to have a higher matching score at another, incorrect location on the Reference Sequence.

FIGS. 6C-6D exemplify alignment of an unknown rare variant near a known structural variant using a DAG reference construct of the invention. FIG. 6C illustrates a DAG that incorporates sequencing data from both the Reference Sequence S and Sequence S*. The DAG Reference Construct 1, as shown in FIG. 6C, includes a reference path (1) that follows the sequence variant common to the Reference Sequence S, and reference path (2) that follows the known structural variant present in Sequences S* and S but uncommon to Reference Sequence S. FIG. 6D illustrates the alignment of Read 1 of S to the DAG Reference Construct 1. As shown, Read 1 aligns almost perfectly with the DAG because Read 1 follows the path with the known structural variant. The only mismatch between Read 1 and the DAG Reference Construct 1 is the rare variant at position 23 (i.e. the T substitution at position 23). Due to the minor mismatch, the alignment algorithm will most likely align Read 1 to the correct location, and such alignment will score above quality thresholds. This alignment allows one to reliably identify the rare variant in Sequence S** due to the high quality of the sequence score. By virtue of being a part of an otherwise well-aligned and high scoring read, the alignment of Read 1 to the DAG Reference Construct 1 allows one to identify the unknown rare variant at position 23 as a legitimate mutation and not as a sequencing error.

Figure 6F:
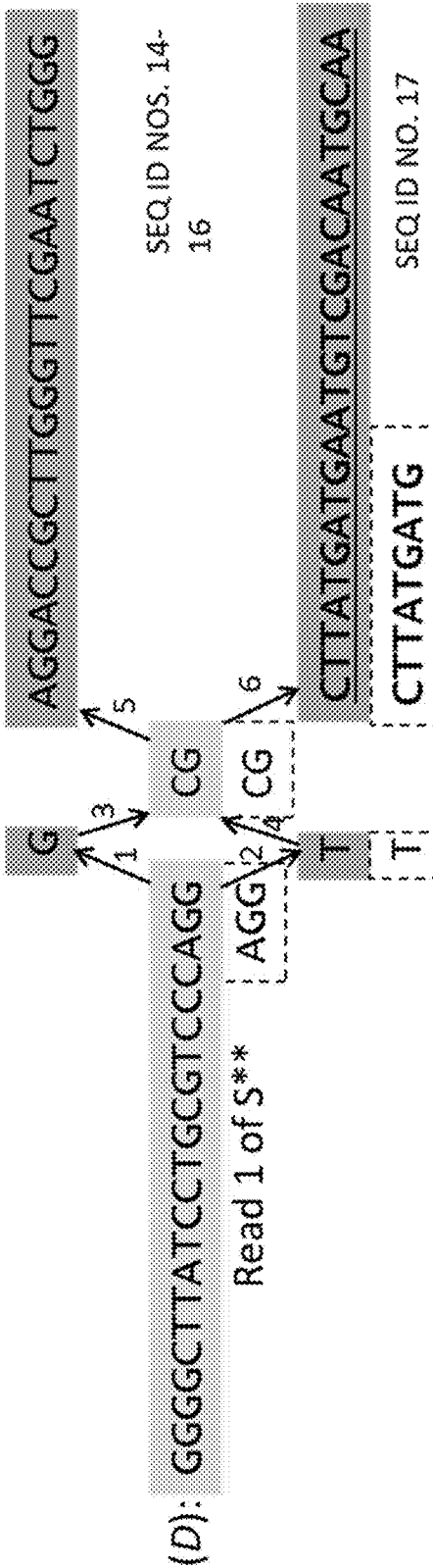
FIG. 6F illustrates alignment of the read to the DAG incorporating all three of the sequences from FIG. 6A.

FIGS. 6E-6F exemplify alignment of a known rare variant near a known structural variant using a DAG reference constructs of the invention. As shown in FIG. 6E, the DAG includes reference paths (1) and (2) to account for the variants in the reference construct due to the G-T substitution at position 23 of the reference sequence, and references paths (3) and (4) to account for the variants in the reference construct due to the known structural variant ranging from position 26 to position 50.

Opportunities for Parallelization

The sequential version of the Smith-Waterman-Gotoh algorithm has been adapted and significantly modified for massive parallelization. For example, an ASC model, called Smith-Waterman using Associative Massive Parallelism (SWAMP) is described in U.S. Patent Publication No. 2012/0239706, incorporated herein by reference in its entirety. Part of the parallelization for SWAMP (and other parallel processing systems) stems from the fact that the values along any anti-diagonal are independent of each other. Thus, all of the cells along a given anti-diagonal can be done in parallel to distribute the computational resources. The data dependencies shown in the above recursive equations limit the level of achievable parallelism but using a wavefront approach will still speed up this useful algorithm. A wavefront approach implemented by Wozniak (*Comput Appl in the Biosciences* (*CABIOS*), 13(2):145-150, 1997) on the Sun Ultra SPARC uses specialized SIMD-like video instructions. Wozniak used the SIMD registers to store the values parallel to the minor diagonal, reporting a two-fold speedup over a traditional implementation on the same machine. Following Wozniak's example, a similar way to parallelize code is to use the Streaming SIMD Extension (SSE) set for the x86 architecture. Designed by Intel, the vector-like operations complete a single operation/instruction on a small number of values (usually four, eight or sixteen) at a time. Many AMD and Intel chips support the various versions of SSE, and Intel has continued developing this technology with the Advanced Vector Extensions (AVX) for their modern chipsets.

In other implementations. Rognes and Seeberg (*Bioinformatics* (Oxford, England), 16(8):699-706, 2000) use the Intel Pentium processor with SSE's predecessor, MMX SIMD instructions for their implementation. The approach that developed out of the work of Rognes and Seeberg (Bioinformatics, 16(8):699-706, 2000) for ParAlign does not use the wavefront approach (Rognes, *Nuc Acids Res,* 29(7):1647-52, 2001; Saebo et al., *Nuc Acids Res.* 33(suppl 2):W535-W539, 2005). Instead, they align the SIMD registers parallel to the query sequence, computing eight values at a time, using a pre-computed query-specific score matrix. Additional details of this method can be found in U.S. Pat. No. 7,917,302, incorporated by reference herein. The way Rognes and Seeberg layout the SIMD registers, the north neighbor dependency could remove up to one third of the potential speedup gained from the SSE parallel "vector" calculations. To overcome this, they incorporate SWAT-like optimizations. With large affine gap penalties, the northern neighbor will be zero most of the time. If this is true, the program can skip computing the value of the north neighbor, referred to as the "lazy F evaluation" by Farrar (Bioinformatics, 23(2):156-161, 2007). Rognes and Seeberg are able to reduce the number of calculations of Equation 1 to speed up their algorithm by skipping it when it is below a certain threshold. A six-fold speedup was reported in (Rognes and Seeberg, *Bioinformatics,* 16(8):699-706, 2000) using 8-way vectors via the MMX/SSE instructions and the SWAT-like extensions.

In the SSE work done by Farrar (*Bioinformatics*, 23(2): 156-161, 2007), a striped or strided pattern of access is used to line up the SIMD registers parallel to the query registers. Doing so avoids any overlapping dependencies. Again incorporating the SWAT-like optimizations (Farrar, *Bioinformatics* 23(2):156-161, 2007) achieves a 2-8 time speedup over Wozniak (*CABIOS* 13(2):145-150, 1997) and Rognes and Seeberg (*Bioinformatics* (Oxford, England), 16(8):699-706, 2000) SIMD implementations. The block substitution matrices and efficient and clever inner loop with the northern (F) conditional moved outside of that inner loop are important optimizations. The strided memory pattern access of the sixteen, 8-bit elements for processing improves the memory access time as well, contributing to the overall speedup.

Farrar (Sequence Analysis, 2008) extended his work for a Cell Processor manufactured by Sony, Toshiba and IBM. This Cell Processor has one main core and eight minor cores. The Cell Broadband Engine was the development platform for several more Smith-Waterman implementations including SWPS3 by Szalkowski, et. al (*BMC Res Notes* 1(107), 2008) and CBFSW by Wirawan, et. al (*BMC Bioinformatics* 9 (377) 2008) both using Farrar's striping approach. Rudnicki, et. al. (*Fund Inform.* 96, 181-194, 2009) used the PS3 to develop a method that used parallelization over multiple databases sequences.

Rognes (*BMC Bioinformatics* 12 (221), 2011) also developed a multi-threaded approach called SWIPE that processes multiple database sequences in parallel. The focus was to use a SIMD approach on "ordinary CPUs." This investigation using coarse-grained parallelism split the work using multiple database sequences in parallel is similar to the graphics processor units (GPU)-based tools described in the CUDASW by Liu, et al. (*BMC Res Notes* 2(73), 2009) and Ligowski and Rudnicki (*Eight Annual International Workshop on High Performance Computational Biology*, Rome, 2009). There have been other implementations of GPU work with CUDASW++2.0 by Liu, et. al. (*BMC Res Notes* 3(93), 2010) and Ligowski, et. al (*GPU Computing Gems, Emerald Edition*, Morgan Kaufmann, 155-157, 2011).

In other variations, small-scale vector parallelization (8, 16 or 32-way parallelism) can be used to make the calculations accessible via GPU implementations that align multiple sequences in parallel. The theoretical peak speedup for the calculations is a factor of m, which is optimal. A 96-fold speedup for the ClearSpeed implementation using 96 processing elements, confirming the theoretical speedup.

Parallel Computing Models

The main parallel model used to develop and extend Smith-Waterman sequence alignment is the ASsociative Computing (ASC) (Potter et al., *Computer*, 27(11):19-25, 1994). Efficient parallel versions of the Smith-Waterman algorithm are described herein. This model and one other model are described in detail in this section.

Some relevant vocabulary is defined here. Two terms of interest from Flynn's Taxonomy of computer architectures are MIMD and SIMD, two different models of parallel computing. A cluster of computers, classified as a multiple-instruction, multiple-data (MIMD) model is used as a proof-of-concept to overcome memory limitations in extremely large-scale alignments. Section 8 describes usage of the MIMD model. An extended data-parallel, single-instruction multiple-data (SIMD) model known as ASC is also described.

Multiple Instruction, Multiple Data (MIMD)

The multiple-data, multiple-instruction model or MIMD model describes the majority of parallel systems currently available, and include the currently popular cluster of computers. The MIMD processors have a full-fledged central processing unit (CPU), each with its own local memory (Quinn, *Parallel Computing: Theory and Practice.* 2nd ed., New York: McGraw-Hill, 1994). In contrast to the SLMD model, each of the MIMD processors stores and executes its own program asynchronously. The MIMD processors are connected via a network that allows them to communicate but the network used can vary widely, ranging from an Ethernet, Myrinet, and InfiniBand connection between machines (cluster nodes). The communications tend to employ a much looser communications structure than SIMDs, going outside of a single unit. The data is moved along the network asynchronously by individual processors under the control of their individual program they are executing. Typically, communication is handled by one of several different parallel languages that support message-passing. A very common library for this is known as the Message Passing Interface (MPI). Communication in a "SIMD-like" fashion is possible, but the data movements will be asynchronous. Parallel computations by MIMDs usually require extensive communication and frequent synchronizations unless the various tasks being executed by the processors are highly independent (i.e. the so-called "embarrassingly parallel" or "pleasingly parallel" problems). The work presented in Section 8 uses an AMD Opteron cluster connected via InfiniBand.

Unlike SIMDs, the worst-case time required for the message-passing is difficult or impossible to predict. Typically, the message-passing execution time for MIMD software is determined using the average case estimates, which are often determined by trial, rather than by a worst case theoretical evaluation, which is typical for SIMDs. Since the worst case for MIMD software is often very bad and rarely occurs, average case estimates are much more useful. As a result, the communication time required for a MIMD on a particular problem can be and is usually significantly higher than for a SIMD. This leads to the important goal in MIMD programming (especially when message-passing is used) to minimize the number of inter-processor communications required and to maximize the amount of time between processor communications. This is true even at a single card acceleration level, such as using graphics processors or GPUs.

Data-parallel programming is also an important technique for MIMD programming, but here all the tasks perform the same operation on different data and are only synchronized at various critical points. The majority of algorithms for MIMD systems are written in the Single-Program, Multiple-Data (SPMD) programming paradigm. Each processor has its own copy of the same program, executing the sections of the code specific to that processor or core on its local data. The popularity of the SPMD paradigm stems from the fact that it is quite difficult to write a large number of different programs that will be executed concurrently across different processors and still be able to cooperate on solving a single problem. Another approach used for memory-intensive but not compute-intensive problems is to create a virtual memory server, as is done with JumboMem, using the work presented in Section 8. This uses MPI in its underlying implementation.

Single Instruction, Multiple Data (SIMD)

The SIMD model consists of multiple, simple arithmetic processing elements called PEs. Each PE has its own local memory that it can fetch and store from, but it does not have the ability to compile or execute a program. As used herein, the term "parallel memory" refers to the local memories, collectively, in a computing system. For example, a parallel memory can be the collective of local memories in a SIMD computer system (e.g., the local memories of PEs), the collective of local memories of the processors in a MIMD computer system (e.g., the local memories of the central processing units) and the like. The compilation and execution of programs are handled by a processor called a control unit (or front end) (Quinn, *Parallel Computing: Theory and Practice,* 2nd ed., New York: McGraw-Hill, 1994). The control unit is connected to all PEs, usually by a bus.

All active PEs execute the program instructions received from the control unit synchronously in lockstep. "In any time unit, a single operation is in the same state of execution on multiple processing units, each manipulating different data" (Quinn, *Parallel Computing: Theory and Practice,* 2nd ed., New York: McGraw-Hill, 1994), at page 79. While the same instruction is executed at the same time in parallel by all active PEs, some PEs may be allowed to skip any particular instruction (Baker, SIMD and MASC: Course notes from CS 6/73301: Parallel and Distributed Computing—power point slides, (2004)2004). This is usually accomplished using an "if-else" branch structure where some of the PEs execute the if instructions and the remaining PEs execute the else part. This model is ideal for problems that are "data-parallel" in nature that have at most a small number of if-else branching structures that can occur simultaneously, such as image processing and matrix operations.

Data can be broadcast to all active PEs by the control unit and the control unit can also obtain data values from a particular PE using the connection (usually a bus) between the control unit and the PEs. Additionally, the set of PE are connected by an interconnection network, such as a linear array, 2-D mesh, or hypercube that provides parallel data movement between the PEs. Data is moved through this network in synchronous parallel fashion by the PEs, which execute the instructions including data movement, in lockstep. It is the control unit that broadcasts the instructions to the PEs. In particular, the SIMD network does not use the message-passing paradigm used by most parallel computers today. An important advantage of this is that SIMD network communication is extremely efficient and the maximum time required for the communication can be determined by the worst-case time of the algorithm controlling that particular communication.

The remainder of this section is devoted to describing the extended SIMD ASC model. ASC is at the center of the algorithm design and development for this discussion.

Associative Computing Model

The ASsocative Computing (ASC) model is an extended SIMD based on the STARAN associative SIMD computer, designed by Dr. Kenneth Batcher at Goodyear Aerospace and its heavily Navy-utilized successor, the ASPRO.

Developed within the Department of Computer Science at Kent State University, ASC is an algorithmic model for associative computing (Potter et al., Computer, 27(11):19-25, 1994) (Potter, *Associative Computing: A Programming Paradigm for Massively Parallel Computers,* Plenum Publishing, 1992). The ASC model grew out of work on the STARAN and MPP, associative processors built by Goodyear Aerospace. Although it is not currently supported in hardware, current research efforts are being made to both efficiently simulate and design a computer for this model.

As an extended SIMD model, ASC uses synchronous data-parallel programming, avoiding both multi-tasking and asynchronous point-to-point communication routing. Multi-tasking is unnecessary since only one task is executed at any time, with multiple instances of this task executed in lockstep on all active processing elements (PEs). ASC, like SIMD programmers, avoid problems involving load balancing, synchronization, and dynamic task scheduling, issues that must be explicitly handled in MPI and other MIMD cluster paradigms.

Figure 4:
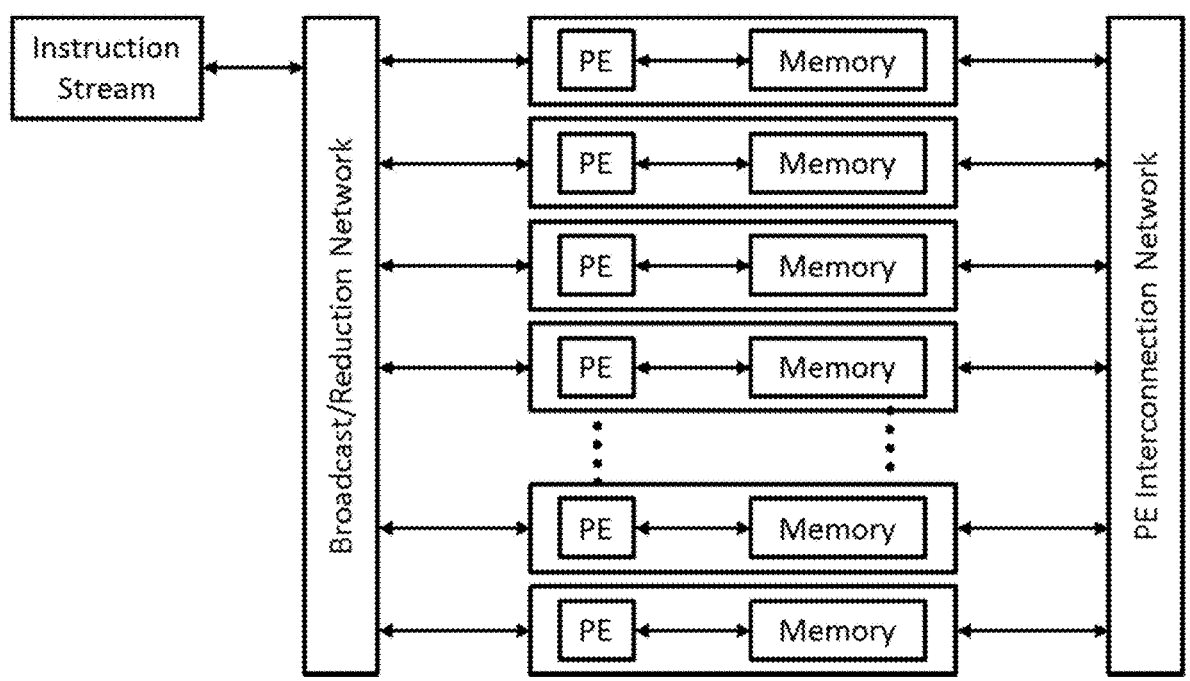
FIG. 4 depicts an associative computing model for parallel processing.

FIG. 4 shows a conceptual model of an ASC computer. There is a single control unit, also known as an instruction stream (IS), and multiple processing elements (PEs), each with its own local memory. The control unit and PE array are connected through a broadcast/reduction network and the PEs are connected together through a PE data interconnection network.

As seen in FIG. 4, a PE has access to data located in its own local memory. The data remains in place and responding (active) PEs process their local data in parallel. The reference to the word associative is related to the use of searching to locate data by content rather than memory addresses. The ASC model does not employ associative memory, instead it is an associative processor where the general cycle is to search-process-retrieve. An overview of the model is available in (Potter et al., *Computer,* 27(11): 19-25, 1994).

The tabular nature of the algorithm lends itself to computation using ASC due to the natural tabular structure of ASC data structures. Highly efficient communication across the PE interconnection network for the lockstep shifting of data of the north and northwest neighbors, and the fast constant time associative functions for searching and for maximums across the parallel computations are well utilized by SWAMP The associative operations are executed in constant time (Jin et al., *15th International Parallel and Distributed Processing Symposium* (IPDPS'01) Workshops, San Francisco, p. 193, 2001), due to additional hardware required by the ASC model. These operations can be performed efficiently (but less rapidly) by any SIMD-like machine, and has been successfully adapted to run efficiently on several SIMD hardware platforms (Yuan et al., *Parallel and Distributed Computing Systems* (PDCS), Cambridge, MA, 2009: Trahan et al., *J. of Parallel and Distributed Computing* (JPDC), 2009). SWAMP and other ASC algorithms can therefore be efficiently implemented on other systems that are closely related to SIMDs including vector machines, which is why the model is used as a paradigm.

The control unit fetches and decodes program instructions and broadcasts control signals to the PEs. The PEs, under the direction of the control unit, execute these instructions using their own local data. All PEs execute instructions in a lockstep manner, with an implicit synchronization between instructions. ASC has several relevant high-speed global operations: associative search, maximum/minimum search, and responder selection/detection. These are described in the following section.

Associative Functions

The functions relevant to the SWAMP algorithms are discussed below. Associative Search The basic operation in an ASC algorithm is the associative search. An associative search simultaneously locates the PEs whose local data matches a given search key. Those PEs that have matching data are called responders and those with non-matching data are called non-responders. After performing a search, the algorithm can then restrict further processing to only affect the responders by disabling the non-responders (or vice versa). Performing additional searches may further refine the set of responders. Associative search is heavily utilized by SWAMP+ in selecting which PEs are active within a parallel act within a diagonal.

Maximum/Minimum Search

In addition to simple searches, where each PE compares its local data against a search key using a standard comparison operator (equal, less than, etc.), an associative computer can also perform global searches, where data from the entire PE array is combined together to determine the set of responders. The most common type of global search is the maximum/minimum search, where the responders are those PEs whose data is the maximum or minimum value across the entire PE array. The maximum value is used by SWAMP+ in every diagonal it processes to track the highest value calculated so far. Use of the maximum search occurs frequently, once in a logical parallel act, m+n times per alignment.

Responder Selection/Detection

An associative search can result in multiple responders and an associative algorithm can process those responders in one of three different modes: parallel, sequential, or single selection. Parallel responder processing performs the same set of operations on each responder simultaneously. Sequential responder processing selects each responder individually, allowing a different set of operations for each responder. Single responder selection (also known as pick-One) selects one, arbitrarily chosen, responder to undergo processing. In addition to multiple responders, it is also possible for an associative search to result in no responders. To handle this case, the ASC model can detect whether there were any responders to a search and perform a separate set of actions in that case (known as anyResponders). In SWAMP, multiple responders that contain characters to be aligned are selected and processed in parallel, based on the associative searches mentioned above. Single responder selection occurs if and when there are multiple values that have the exact same maximum value when using the maximum/minimum search.

PE Interconnection Network

Most associative processors include some type of PE interconnection network to allow parallel data movement within the array. The ASC model itself does not specify any particular interconnection network and, in fact, many useful associative algorithms do not require one. Typically associative processors implement simple networks such as 1D linear arrays or 2D meshes. These networks are simple to implement and allow data to be transferred quickly in a synchronous manner. The 1D linear array is sufficient for the explicit communication between PEs in the SWAMP algorithms, for example.

Parallel Computing Systems

Figure 5:
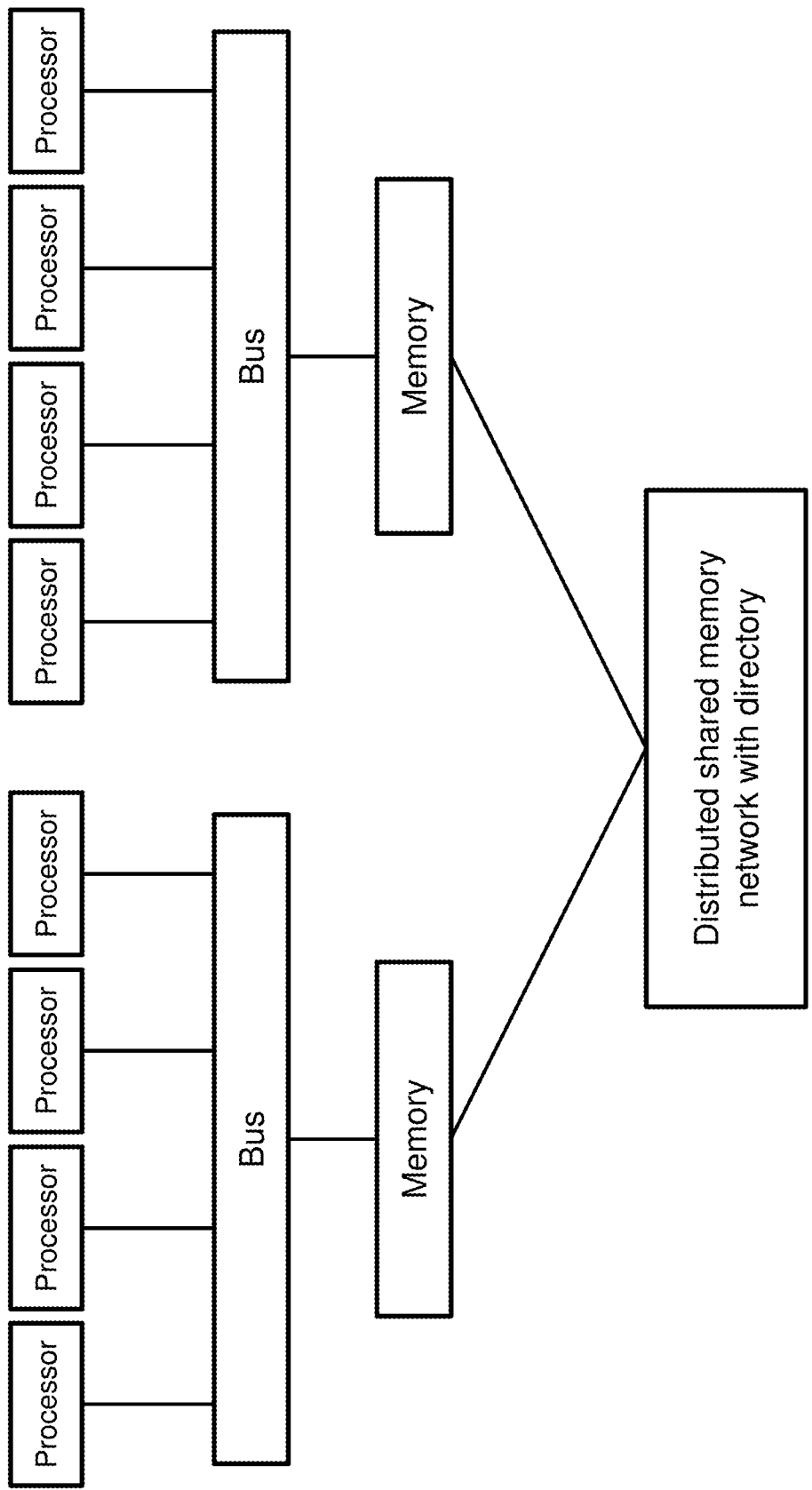
FIG. 5 depicts an architecture for parallel computation.

A generalized parallel processing architecture is shown in FIG. 5. While each component is shown as having a direct connection, it is to be understood that the various elements may be geographically separated but connected via a network, e.g., the internet. While hybrid configurations are possible, the main memory in a parallel computer is typically either shared between all processing elements in a single address space, or distributed, i.e., each processing element has its own local address space. (Distributed memory refers to the fact that the memory is logically distributed, but often implies that it is physically distributed as well.) Distributed shared memory and memory virtualization combine the two approaches, where the processing element has its own local memory and access to the memory on non-local processors. Accesses to local memory are typically faster than accesses to non-local memory.

Computer architectures in which each element of main memory can be accessed with equal latency and bandwidth are known as Uniform Memory Access (UMA) systems. Typically, that can be achieved only by a shared memory system, in which the memory is not physically distributed. A system that does not have this property is known as a Non-Uniform Memory Access (NUMA) architecture. Distributed memory systems have non-uniform memory access.

Processor-processor and processor-memory communication can be implemented in hardware in several ways, including via shared (either multiported or multiplexed) memory, a crossbar switch, a shared bus or an interconnect network of a myriad of topologies including star, ring, tree, hypercube, fat hypercube (a hypercube with mom than one processor at a node), or n-dimensional mesh.

Parallel computers based on interconnected networks must incorporate routing to enable the passing of messages between nodes that are not directly connected. The medium used for communication between the processors is likely to be hierarchical in large multiprocessor machines. Such resources are commercially available for purchase for dedicated use, or these resources can be accessed via "the cloud," e.g., Amazon Cloud Computing.

A computer generally includes a processor coupled to a memory via a bus. Memory can include RAM or ROM and preferably includes at least one tangible, non-transitory medium storing instructions executable to cause the system to perform functions described herein. As one skilled in the art would recognize as necessary or best-suited for performance of the methods of the invention, systems of the invention include one or more processors (e.g., a central processing unit (CPU), a graphics processing unit (GPU), etc.), computer-readable storage devices (e.g., main memory, static memory, etc.), or combinations thereof which communicate with each other via a bus.

A processor may be any suitable processor known in the art, such as the processor sold under the trademark XEON E7 by Intel (Santa Clara, CA) or the processor sold under the trademark OPTERON 6200 by AMD (Sunnyvale, CA).

Memory may refer to a computer-readable storage device and can include any machine-readable medium on which is stored one or more sets of instructions (e.g., software embodying any methodology or function found herein), data (e.g., embodying any tangible physical objects such as the genetic sequences found in a patient's chromosomes), or both. While the computer-readable storage device can in an exemplary embodiment be a single medium, the term "computer-readable storage device" should be taken to include a single medium or multiple media (e.g., a centralized or distributed database, and/or associated caches and servers) that store the one or more sets of instructions or data. The term "computer-readable storage device" shall accordingly be taken to include, without limit, solid-state memories (e.g., subscriber identity module (STM) card, secure digital card (SD card), micro SD card, or solid-state drive (SSD)), optical and magnetic media, and any other tangible storage media. Preferably, a computer-readable storage device includes a tangible, non-transitory medium. Such non-transitory media excludes, for example, transitory waves and signals. "Non-transitory memory" should be interpreted to exclude computer readable transmission media, such as signals, per se.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Sample Acquisition and Preparation

The invention includes methods for producing sequences (e.g., nucleic acid sequences, amino acid sequences) corresponding to nucleic acids recovered from biological samples. In some embodiments the resulting information can be used to identify mutations present in nucleic acid material obtained from a subject. In some embodiments, a sample, i.e., nucleic acids (e.g. DNA or RNA) are obtained from a subject, the nucleic acids are processed (lysed, amplified, and/or purified) and the nucleic acids are sequenced using a method described below. In many embodiments, the result of the sequencing is not a linear nucleic acid sequence, but a collection of thousands or millions of individual short nucleic acid reads that must be re-assembled into a sequence for the subject. Once the reads are aligned to produce a sequence, the aligned sequence can be compared to reference sequences to identify mutations that may be indicative of disease, for example. In other embodiments, the subject may be identified with particular mutations based upon the alignment of the reads against a reference sequence construct, i.e., a directed acyclic graph ("DAG") as described above.

For any of the above purposes, methods may be applied to biological samples. The biological samples may, for example, comprise samples of blood, whole blood, blood plasma, tears, nipple aspirate, serum, stool, urine, saliva, circulating cells, tissue, biopsy samples, hair follicle or other samples containing biological material of the patient. One issue in conducting tests based on such samples is that, in most cases only a tiny amount of DNA or RNA containing a mutation of interest may be present in a sample. This is especially true in non-invasive samples, such as a buccal swab or a blood sample, where the mutant nucleic acids are present in very small amounts. In some embodiments, the nucleic acid fragments may be naturally short, that is, random shearing of relevant nucleic acids in the sample can generate short fragments. In other embodiments, the nucleic acids are purposely fragmented for ease of processing or because the sequencing techniques can only sequence reads of less than 1000 bases, e.g., less than 500 bases, e.g., less than 200 bases, e.g., less than 100 bases, e.g., less than 50 bases. While the methods described herein can be used to align sequences of varying length, in some embodiments, the majority of the plurality of nucleic acid reads will follow from the sequencing method and comprise less than 1000 bases, e.g., less than 500 bases, e.g., less than 200 bases, e.g., less than 100 bases, e.g., less than 50 bases.

Nucleic acids may be obtained by methods known in the art. Generally, nucleic acids can be extracted from a biological sample by a variety of techniques such as those described by Maniatis, et al., Molecular Cloning: A Laboratory Manual, Cold Spring Harbor, N.Y., pp. 280-281 (1982), the contents of which is incorporated by reference herein in its entirety.

It may be necessary to first prepare an extract of the sample and then perform further steps—i.e., differential precipitation, column chromatography, extraction with organic solvents and the like—in order to obtain a sufficiently pure preparation of nucleic acid. Extracts may be prepared using standard techniques in the art, for example, by chemical or mechanical lysis of the cell. Extracts then may be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. In some embodiments, the sample may comprise RNA, e.g., mRNA, collected from a subject sample, e.g., a blood sample. General methods for RNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). The contents of each of these references is incorporated by reference herein in their entirety. In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE Complete DNA and RNA Purification Kit (EPICENTRE, Madison. Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

Analytical Sequencing

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes. Prior to sequencing it may be additionally beneficial to amplify some or all of the nucleic acids in the sample. In some embodiments, the nucleic acids are amplified using polymerase chain reactions (PCR) techniques known in the art.

One example of a sequencing technology that can be used in the methods of the provided invention is Illumina sequencing (e.g., the MiSeq™ platform), which is a polymerase-based sequence-by-synthesis that may be utilized to amplify DNA or RNA. Illumina sequencing for DNA is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. When using Illumina sequencing to detect RNA the same method applies except RNA fragments are being isolated and amplified in order to determine the RNA expression of the sample. After the sequences are interrogated with the sequencer, they may be output in a data file, such as a FASTQ file, which is a text-based format for storing biological sequence and quality scores (see discussion above).

Another example of a DNA sequencing technique that may be used in the methods of the provided invention is Ion Torrent™ sequencing, offered by Life Technologies. See U.S. patent application numbers 2009/0026082.2009/0127589, 2010/0035252, 2010/0137143, 2010/0188073, 2010/0197507, 2010/0282617, 2010/0300559, 2010/0300895, 2010/0301398, and 201010304982, the content of each of which is incorporated by reference herein in its entirety. In Ion Torren™ sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton (H'), which signal detected and recorded in a sequencing instrument. The signal strength is proportional to the number of nucleotides incorporated. Ion Torrent data may also be output as a FASTQ file.

Another example of a DNA and RNA sequencing technique that can be used in the methods of the provided invention is 454™ sequencing (Roche) (Margulies, M et al. 2005, Nature, 437, 376-380). 454™ sequencing is a sequencing-by-synthesis technology that utilizes also utilizes pyrosequencing. 454™ sequencing of DNA involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed. In another embodiment, pyrosequencing is used to measure gene expression. Pyrosequecing of RNA applies similar to pyrosequencing of DNA, and is accomplished by attaching applications of partial rRNA gene sequencings to microscopic beads and then placing the attachments into individual wells. The attached partial rRNA sequence are then amplified in order to determine the gene expression profile. Sharon Marsh, *Pyrosequencing® Protocols in Methods in Molecular Biology*, Vol. 373, 15-23 (2007).

Another example of a DNA and RNA detection techniques that may be used in the methods of the provided invention is SOLiD™ technology (Applied Biosystems). SOLiD™ technology systems is a ligation based sequencing technology that may utilized to run massively parallel next generation sequencing of both DNA and RNA. In DNA SOLiD™ sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In other embodiments, SOLiD™ Serial Analysis of Gene Expression (SAGE) is used to measure gene expression. Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997, the contents of each of which are incorporated by reference herein in their entirety).

Another sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™, sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et at. (U.S. Pat. No. 7,169,560), Lapidus et at. (U.S. patent application number 2009/0191565), Quake et al. (U.S. Pat. No. 6,818,395), Harris (U.S. Pat. No. 7,282,337). Quake et al. (U.S. patent application number 2002/0164629), and Braslavsky, et al., PNAS (USA), 100: 3960-3964 (2003), the contents of each of these references is incorporated by reference herein in its entirety.

Another example of a sequencing technology that may be used in the methods of the provided invention includes the single molecule, real-time (SMRT) technology of Pacific Biosciences to sequence both DNA and RNA. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated. In order to sequence RNA, the DNA polymerase is replaced with a with a reverse transcriptase in the ZMW, and the process is followed accordingly.

Another example of a sequencing technique that can be used in the methods of the provided invention is nanopore sequencing (Soni G V and Meller, AClin Chem 53: 1996-2001) (2007). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using an electron microscope (Moudrianakis E. N. and Beer M. Proc Natd Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Additional detection methods can utilize binding to microarrays for subsequent fluorescent or non-fluorescent detection, barcode mass detection using a mass spectrometric methods, detection of emitted radiowaves, detection of scattered light from aligned barcodes, fluorescence detection using quantitative PCR or digital PCR methods. A comparative nucleic acid hybridization array is a technique for detecting copy number variations within the patient's sample DNA. The sample DNA and a reference DNA are differently labeled using distinct fluorophores, for example, and then hybridized to numerous probes. The fluorescent intensity of the sample and reference is then measured, and the fluorescent intensity ratio is then used to calculate copy number variations. Methods of comparative genomic hybridization array are discussed in more detail in Shinawi M. Cheung S W *The array CGH and its clinical applications*, Drug Discovery Today 13 (17-18): 760-70. Microarray detection may not produce a FASTQ file directly, however programs are available to convert the data produced by the microarray sequencers to a FASTQ, or similar, format.

Another method of detecting DNA molecules, RNA molecules, and copy number is fluorescent in situ hybridization (FISH). In Situ Hybridization Protocols (Ian Darby ed., 2000). FISH is a molecularcytogenetic technique that detects specific chromosomal rearrangements such as mutations in a DNA sequence and copy number variances. A DNA molecule is chemically denatured and separated into two strands. A single stranded probe is then incubated with a denatured strand of the DNA. The signals stranded probe is selected depending target sequence portion and has a high affinity to the complementary sequence portion. Probes may include a repetitive sequence probe, a whole chromosome probe, and locus-specific probes. While incubating, the combined probe and DNA strand are hybridized. The results are then visualized and quantified under a microscope in order to assess any variations.

In another embodiment, a MassARRAY™-based gene expression profiling method is used to measure gene expression. In the MassARRAY™-based gene expression profiling method, developed by Sequenom. Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization Lime-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059 3064 (2003).

Further PCR-based techniques include, for example, differential display (Liang and Pardee, Science 257:967 971 (1992)); amplified fragment length polymorphism (iAFLP) (Kawamoto et aL, Genome Res. 12:1305 1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); Beads Array for Detection of Gene Expression (BADGE), using the commercially available Luminex100 LabMAP system and multiple color-coded microspheres (Luminex Corp., Austin. Tex.) in a rapid assay for gene expression (Yang et al., Genome Res. 11:1888 1898 (2001)); and high coverage expression profiling (HiCEP) analysis (Fukumura et al., Nucl. Acids. Res. 31(16) e94 (2003)). The contents of each of which are incorporated by reference herein in their entirety.

In certain embodiments, variances in gene expression can also be identified, or confirmed using a microarray techniques, including nylon membrane arrays, microchip arrays and glass slide arrays, e.g., such as available commercially from Affymetrix (Santa Clara, CA). Generally, RNA samples are isolated and converted into labeled cDNA via reverse transcription. The labeled cDNA is then hybridized onto either a nylon membrane, microchip, or a glass slide with specific DNA probes from cells or tissues of interest. The hybridized cDNA is then detected and quantified, and the resulting gene expression data may be compared to controls for analysis. The methods of labeling, hybridization, and detection vary depending on whether the microarray support is a nylon membrane, microchip, or glass slide. Nylon membrane arrays are typically hybridized with P-dNTP labeled probes. Glass slide arrays typically involve labeling with two distinct fluorescently labeled nucleotides. Methods for making microarrays and determining gene product expression (e.g., RNA or protein) are shown in Yeatman et al. (U.S. patent application number 2006/0195269), the content of which is incorporated by reference herein in its entirety.

In some embodiments, mass spectrometry (MS) analysis can be used alone or in combination with other methods (e.g., immunoassays or RNA measuring assays) to determine the presence and/or quantity of the one or more biomarkers disclosed herein in a biological sample. In some embodiments, the MS analysis includes matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated by reference herein in their entirety.

Protein sequences for use with the methods, sequence constructs, and systems of the invention can be determined using a number of techniques known to those skilled in the relevant art. For example, amino acid sequences and amino acid sequence reads may be produced by analyzing a protein or a portion of a protein with mass spectrometry or using Edman degradation. Mass spectrometry may include, for example, matrix-assisted laser desorption/ionization (MALDI) time-of-flight (TOF) MS analysis, such as for example direct-spot MALDI-TOF or liquid chromatography MALDI-TOF mass spectrometry analysis, electrospray ionization (ESI) MS, such as for example liquid chromatography (LC) ESI-MS, or other techniques such as MS-MS. Edman degradation analysis may be performed using commercial instruments such as the Model 49X Procise protein/peptide sequencer (Applied Biosystems/Life Technologies). The sequenced amino acid sequences, i.e., polypeptides, i.e., proteins, may be at least 10 amino acids in length, e.g., at least 20 amino acids in length, e.g., at least 50 amino acids in length.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for identifying a genomic variant as present in a nucleic acid sample, the method comprising:
using at least one processor to perform:
accessing, from at least one non-transitory storage medium, a genomic reference graph representing at least a portion of a genome of an organism and genetic variation of at least the portion of the genome of the organism, the portion of the genome comprising greater than 1,000,000 nucleic acids, and the genomic reference graph comprising nodes and edges, wherein a first path through the genomic reference graph represents at least the portion of the genome of the organism, and wherein a second path through the genomic reference graph represents at least some of the genetic variation of at least the portion of the genome of the organism, the second path including a first node representing a first genomic variant;
obtaining one or more nucleic acid sequence reads associated with the nucleic acid sample;
aligning the one or more nucleic acid sequence reads to the genomic reference graph representing at least the portion of the genome of the organism and the genetic variation of at least the portion of the genome of the organism using a dynamic programming algorithm, the aligning comprising, for a nucleic acid sequence read of the one or more nucleic acid sequence reads:
determining overlap scores for the nucleic acid sequence read against the genomic reference graph; and
aligning the nucleic acid sequence read to the genomic reference graph based on the overlap scores; and
identifying the first genomic variant as present in the nucleic acid sample based on results of the aligning the one or more nucleic acid sequence reads to the genomic reference graph representing at least the portion of the genome of the organism and the genetic variation of at least the portion of the genome of the organism.

2. The method of claim 1,
wherein identifying the first genomic variant as present in the nucleic acid sample comprises:
identifying the first genomic variant as present in the nucleic acid sample when the nucleic acid sequence read aligns, at least partially, to the first node.

3. The method of claim 1,
wherein the first path through the genomic reference graph comprises a second node representing a genomic sequence lacking the first genomic variant, at a same position as the first node in the genomic reference graph.

4. The method of claim 3, wherein the genomic reference graph represents greater than 100,000 10,000,000 nucleic acids.

5. The method of claim 1, wherein the first genomic variant comprises a deletion, duplication, copy-number variation, insertion, inversion, translocation, or any combination thereof.

6. The method of claim 1, further comprising identifying, based on the results of the aligning, a second genomic variant, wherein the second genomic variant is not represented by the genomic reference graph.

7. The method of claim 6, wherein the second genomic variant comprises a single nucleotide polymorphism.

8. The method of claim 1, wherein at least the portion of the genome of the organism comprises at least a portion of a human genome.

9. The method of claim 1, wherein at least the portion of the genome of the organism comprises a chromosome of the organism.

10. A system, comprising:
at least one processor; and
at least one non-transitory storage medium storing processor-executable instructions that, when executed by the at least one processor, cause the at least one processor to perform a method for identifying a genomic variant as present in a nucleic acid sample, the method comprising:
accessing, from the at least one non-transitory storage medium, a genomic reference graph representing at least a portion of a genome of an organism and genetic variation of at least the portion of the genome of the organism, the portion of the genome comprising greater than 1,000,000 nucleic acids, and the genomic reference graph comprising nodes and edges, wherein a first path through the genomic reference graph represents at least the portion of the genome of the organism, and wherein a second path through the genomic reference graph represents at least some of the genetic variation of at least the portion of the genome of the organism, the second path including a first node representing a first genomic variant;
obtaining one or more nucleic acid sequence reads associated with the nucleic acid sample;
aligning the one or more nucleic acid sequence reads to the genomic reference graph representing at least the portion of the genome of the organism and the genetic variation of at least the portion of the genome of the organism using a dynamic programming algorithm, the aligning comprising, for a nucleic acid sequence read of the one or more nucleic acid sequence reads:
determining overlap scores for the nucleic acid sequence read against the genomic reference graph; and aligning the nucleic acid sequence read to the genomic reference graph based on the overlap scores; and identifying the first genomic variant as present in the nucleic acid sample based on results of the aligning the one or more nucleic acid sequence reads to the genomic reference graph representing at least the portion of the genome of the organism and the genetic variation of at least the portion of the genome of the organism.

11. The system of claim 10, wherein identifying the first genomic variant as present in the nucleic acid sample comprises:

identifying the first genomic variant as present in the nucleic acid sample when the nucleic acid sequence read aligns, at least partially, to the first node.

12. The system of claim 10, wherein the first path through the genomic reference graph comprises a second node representing a genomic sequence lacking the first genomic variant, at a same position as the first node in the genomic reference graph.

13. The system of claim 10, wherein the first genomic variant comprises a deletion, duplication, copy-number variation, insertion, inversion, translocation, or any combination thereof.

14. The system of claim 10, further comprising identifying, based on the results of the aligning, a second genomic variant, wherein the second genomic variant is not represented by the genomic reference graph.

15. The system of claim 14, wherein the second genomic variant comprises a single nucleotide polymorphism.

16. At least one non-transitory storage medium storing processor-executable instructions that, when executed by at least one processor, cause the at least one processor to perform a method for identifying a genomic variant as present in a nucleic acid sample, the method comprising:

accessing, from the at least one non-transitory storage medium, a genomic reference graph representing at least a portion of a genome of an organism and genetic variation of at least the portion of the genome of the organism, the portion of the genome comprising greater than 1,000,000 nucleic acids, and the genomic reference graph comprising nodes and edges, wherein a first path through the genomic reference graph represents at least the portion of the genome of the organism, and wherein a second path through the genomic reference graph represents at least some of the genetic variation of at least the portion of the genome of the organism, the second path including a first node representing a first genomic variant;

obtaining one or more nucleic acid sequence reads associated with the nucleic acid sample;

aligning the one or more nucleic acid sequence reads to the genomic reference graph representing at least the portion of the genome of the organism and the genetic variation of at least the portion of the genome of the organism using a dynamic programming algorithm, the aligning comprising, for a nucleic acid sequence read of the one or more nucleic acid sequence reads:

determining overlap scores for the nucleic acid sequence read against the genomic reference graph; and aligning the nucleic acid sequence read to the genomic reference graph based on the overlap scores; and identifying the first genomic variant as present in the nucleic acid sample based on results of the aligning the one or more nucleic acid sequence reads to the genomic reference graph representing at least the portion of the genome of the organism and the genetic variation of at least the portion of the genome of the organism.

17. The at least one non-transitory storage medium of claim 16, wherein identifying the first genomic variant as present in the nucleic acid sample comprises:

identifying the first genomic variant as present in the nucleic acid sample when the nucleic acid sequence read aligns, at least partially, to the first node.

18. The at least one non-transitory storage medium of claim 16, wherein the first path through the genomic reference graph comprises a second node representing a genomic sequence lacking the first genomic variant, at a same position as the first node in the genomic reference graph.

19. The at least one non-transitory storage medium of claim 16, wherein the first genomic variant comprises a deletion, duplication, copy-number variation, insertion, inversion, translocation, or any combination thereof.

20. The at least one non-transitory storage medium of claim 16, further comprising identifying, based on the results of the aligning, a second genomic variant, wherein the second genomic variant is not represented by the genomic reference graph.

* * * * *

UNITED STATES PATENT AND TRADEMARK OFFICE
CERTIFICATE OF CORRECTION

| | |
|---|---|
| PATENT NO. | : 11,837,328 B2 |
| APPLICATION NO. | : 17/933260 |
| DATED | : December 5, 2023 |
| INVENTOR(S) | : Deniz Kural |

It is certified that error appears in the above-identified patent and that said Letters Patent is hereby corrected as shown below:

In the Claims

At Column 36, Line 14:
"graph represents greater than 100,000 10,000,000 nucleic"

Should read:
--graph represents greater than 10,000,000 nucleic--

Signed and Sealed this
Twentieth Day of February, 2024

Katherine Kelly Vidal
*Director of the United States Patent and Trademark Office*